US010287507B2

(12) United States Patent
Ravikumar (10) Patent No.: US 10,287,507 B2
(45) Date of Patent: May 14, 2019

(54) CONVERSION OF WASTE $CO_2$ INTO USEFUL TRANSPORT FUELS USING STEAM METHANE REFORMER IN A GAS TO LIQUIDS PLANT

(71) Applicant: Fluor Technologies Corporation, Sugar Land, TX (US)

(72) Inventor: Ravi Ravikumar, Lancaster, CA (US)

(73) Assignee: Fluor Technologies Corporation, Sugar Land, TX (US)

( * ) Notice: Subject to any disclaimer, the term of this patent is extended or adjusted under 35 U.S.C. 154(b) by 378 days.

(21) Appl. No.: 15/000,559

(22) Filed: Jan. 19, 2016

(65) Prior Publication Data

US 2017/0204335 A1    Jul. 20, 2017

(51) Int. Cl.
*C10G 2/00* (2006.01)
*C07C 1/04* (2006.01)
(Continued)

(52) U.S. Cl.
CPC ............ *C10G 2/32* (2013.01); *C01B 3/48* (2013.01); *C01B 3/56* (2013.01); *C07C 1/04* (2013.01);
(Continued)

(58) Field of Classification Search
CPC ..... C01B 3/48; C01B 3/56; C01B 2203/0233; C01B 2203/0283; C01B 2203/042;
(Continued)

(56) References Cited

U.S. PATENT DOCUMENTS 2,622,089 A * 12/1952 Mayland .................. C01B 3/38
                                                            48/198.7
5,506,272 A *  4/1996 Benham ................... B01J 23/78
                                                              518/700
(Continued)

FOREIGN PATENT DOCUMENTS

CA    3010217 A1    7/2017
EP    0253540 A1    1/1988
(Continued)

OTHER PUBLICATIONS

Patent Cooperation Treaty, "Notification of Transmittal of the International Search Report and the Written Opinion of the International Searching Authority, or the Declaration", PCT Application No. PCT/US/2013/041698, dated May 17, 2013.
(Continued)

*Primary Examiner* — Medhanit W Bahta
(74) *Attorney, Agent, or Firm* — Conley Rose, PC (57) ABSTRACT

A method of producing fuel from $CO_2$ comprising introducing natural gas, steam, and recovered $CO_2$ to a reformer to produce unshifted syngas characterized by a molar ratio of hydrogen to carbon monoxide of from about 1.7:1 to about 2.5:1; introducing the unshifted syngas to a water gas shift unit to produce a shifted syngas, wherein an amount of $CO_2$ in the shifted syngas is greater than in the unshifted syngas; separating the $CO_2$ from the shifted syngas to produce recycle $CO_2$ and a hydrogen-enriched syngas; recycling the recycle $CO_2$ to the reformer; introducing the unshifted syngas to a Fischer-Tropsch (FT) unit to produce an FT product, FT water, and FT tail gas, wherein the FT product comprises FT liquids and FT wax; and separating the FT liquids from the FT product to produce a fuel.

27 Claims, 1 Drawing Sheet

(51) Int. Cl.
*C01B 3/48* (2006.01)
*C01B 3/56* (2006.01)
*C10G 47/00* (2006.01)
*G06Q 30/00* (2012.01)
*C10G 45/00* (2006.01)
*C10K 1/32* (2006.01)
*C10L 1/06* (2006.01)
*C10L 1/08* (2006.01)

(52) U.S. Cl.
CPC ........... *C07C 1/0485* (2013.01); *C10G 45/00* (2013.01); *C10G 47/00* (2013.01); *C10K 1/32* (2013.01); *C10L 1/06* (2013.01); *C10L 1/08* (2013.01); *G06Q 30/018* (2013.01); *C01B 2203/0233* (2013.01); *C01B 2203/0283* (2013.01); *C01B 2203/042* (2013.01); *C01B 2203/0475* (2013.01); *C01B 2203/062* (2013.01); *C01B 2203/1058* (2013.01); *C01B 2203/1241* (2013.01); *C01B 2203/142* (2013.01); *C10G 2300/1022* (2013.01); *C10G 2400/02* (2013.01); *C10G 2400/04* (2013.01); *C10G 2400/08* (2013.01); *C10L 2200/0469* (2013.01); *C10L 2200/0492* (2013.01); *C10L 2290/02* (2013.01); *C10L 2290/10* (2013.01); *C10L 2290/42* (2013.01); *C10L 2290/542* (2013.01); *Y02P 30/10* (2015.11)

(58) Field of Classification Search
CPC ...... C01B 2203/0475; C01B 2203/062; C01B 2203/1058; C01B 2203/1241; C01B 2203/142; C10G 2/32; C10G 45/00; C10G 47/00; C10G 2300/1022; C10G 2400/02; C10G 2400/04; C10G 2400/08; C10K 1/32; C10L 1/06; C10L 1/08; C10L 2200/0469; C10L 2200/0492; C10L 2290/02; C10L 2290/10; C10L 2290/42; C10L 2290/542; G06Q 30/018
See application file for complete search history.

(56) References Cited

U.S. PATENT DOCUMENTS

| | | |
|---|---|---|
| 7,638,070 B2 | 12/2009 | Johnson et al. |
| 7,781,490 B2 | 8/2010 | Lattner et al. |
| 7,857,995 B2 | 12/2010 | Johnson et al. |
| 7,968,006 B2 | 6/2011 | Johnson et al. |
| 8,017,040 B2 | 9/2011 | Johnson et al. |
| 8,017,041 B2 | 9/2011 | Johnson et al. |
| 8,021,577 B2 | 9/2011 | Johnson et al. |
| 8,197,698 B2 | 6/2012 | Johnson et al. |
| 2004/0181313 A1 | 9/2004 | Sergio et al. |
| 2007/0010589 A1 | 1/2007 | Pearson |
| 2007/0259972 A1 | 11/2007 | Lattner et al. |
| 2009/0048354 A1 | 2/2009 | Bell et al. |
| 2009/0069452 A1 | 3/2009 | Robota |
| 2009/0186952 A1 | 7/2009 | Steynberg et al. |
| 2009/0230024 A1 | 9/2009 | Steynberg et al. |
| 2010/0069514 A1 | 3/2010 | Gracey et al. |
| 2010/0175320 A1 | 7/2010 | Schuetzle et al. |
| 2011/0144397 A1 | 6/2011 | van Egmond et al. |
| 2014/0224706 A1 | 8/2014 | Do et al. |
| 2015/0141535 A1 | 5/2015 | Kresnyak |
| 2015/0315019 A1* | 11/2015 | Pontes et al. ............ B01J 23/83 252/373 |

FOREIGN PATENT DOCUMENTS

EP    1916233 A1    4/2008
WO    2005/021421 A2    3/2005

OTHER PUBLICATIONS

International Patent Application No. PCT/US2016/015989, International Preliminary Report on Patentability dated Aug. 2, 2018, 13 pages.

PCT Application No. PCT/US2016/015989, International Search Report and Written Opinion, dated Aug. 24, 2016, 16 pages.

* cited by examiner

CONVERSION OF WASTE CO₂ INTO USEFUL TRANSPORT FUELS USING STEAM METHANE REFORMER IN A GAS TO LIQUIDS PLANT

TECHNICAL FIELD

The present disclosure relates to methods of producing transport fuels from waste carbon dioxide, more specifically converting carbon dioxide into synthesis gas (syngas), wherein the syngas can be used for the production of transport fuels via a Fischer-Tropsch process.

BACKGROUND

Syngas is a mixture comprising primarily of carbon monoxide and hydrogen. Syngas is widely used in industrial settings, either for electricity generation or as an intermediate in the production of synthetic natural gas, hydrogen, ammonia, methanol, and liquid hydrocarbons (e.g., fuels), for example via a Fischer-Tropsch process.

Carbon dioxide ($CO_2$) is the main greenhouse gas emitted through human activities. Many industrial processes emit $CO_2$ through fossil fuel combustion. Several processes also produce $CO_2$ emissions through chemical reactions that do not involve combustion, for example, production and consumption of mineral products such as cement, production of metals such as iron and steel, and production of chemicals. Many industrial processes also use electricity and therefore indirectly cause $CO_2$ emissions from electricity production. Thus, there is an ongoing need for the development of methods for reducing carbon dioxide emissions, for example by converting carbon dioxide into useful products, such as syngas, which can be further converted into fuel.

Also, the 2010 United States federal budget proposed to support clean energy development with a 10-year investment of $15 billion per year, generated from the sale of greenhouse gases (GHG) emissions credits.

Emissions trading schemes are a market-based approach used to control pollution by providing economic incentives for achieving reductions in the emissions of pollutants. Governing entities may establish a limit or cap on the amount of a pollutant that can be emitted. Such limit or cap may be applied, allocated, or sold to entities which have been identified as capable of producing emissions at a level which could be subject to the established limit or cap for said designated pollutants. These limits or caps may be applied, allocated, or sold to such emissions entities in the form of emissions permits which represent the right to emit or discharge a specific volume of a specified pollutant. Such emission producing entities are required to hold a number of permits (or credits) equivalent to their emissions. The total amount of permits (or credits) issued by the governing entity cannot exceed the cap; thus, limiting total emissions to that level. Emissions entities that need to increase their level of emissions must buy permits from those who require fewer permits. The transfer of permits is referred to as a trade. In effect, the buyer is paying a charge for polluting, while the seller is being rewarded for having reduced emissions.

The overall goal of an emissions trading plan is to minimize the cost of meeting a set emissions target. The cap is an enforceable limit on emissions that is usually lowered over time, aiming towards a national emissions reduction target. In other systems, a portion of all traded credits must be retired, causing a net reduction in emissions each time a trade occurs. Thus, in theory, by limiting or capping polluting emissions the totality of pollution may be decreased. Moreover, those who can reduce emissions most cheaply will do so, achieving pollution reduction at the lowest cost to society.

Therefore, emissions trading schemes create a framework by which a carbon offset may be utilized as a carbon credit. A "carbon offset" generally refers to a reduction by an entity in emissions of carbon dioxide or another GHG that is capable of compensating for an emission of carbon dioxide or another GHG elsewhere. Carbon offsets are measured in metric tons of carbon dioxide-equivalent ($CO_2e$) and include various categories of GHGs, among them, carbon dioxide and methane. One carbon offset represents the reduction of one metric ton of carbon dioxide or its equivalent in other greenhouse gases. A "carbon credit" generally refers to a tradable certificate, permit, or other negotiable instrument representing the right to emit one ton of carbon dioxide or the mass of another greenhouse gas having a carbon dioxide equivalency of one metric ton.

There are active trading programs in several air pollutants including carbon credits. Thus, a system or method that may be operated so as to yield an overall reduction in emissions in the amount of carbon dioxide or an equivalent GHG may be economically beneficial.

BRIEF SUMMARY

Disclosed herein is a method of producing fuel from carbon dioxide comprising (a) introducing natural gas, steam, and recovered carbon dioxide to a reformer to produce unshifted synthesis gas (syngas), wherein the unshifted syngas is characterized by a molar ratio of hydrogen to carbon monoxide of from about 1.7:1 to about 2.5:1, and wherein the reformer is a new reformer, an existing reformer, or combinations thereof, (b) introducing a portion of the unshifted syngas to a water gas shift unit to produce a shifted syngas, wherein a molar ratio of hydrogen to carbon monoxide in the shifted syngas is greater than a molar ratio of hydrogen to carbon monoxide in the unshifted syngas, wherein an amount of carbon dioxide in the shifted syngas is greater than an amount of carbon dioxide in the unshifted syngas, and wherein the water gas shift unit is a new water gas shift unit, an existing water gas shift unit, or combinations thereof, (c) separating at least a portion of the carbon dioxide from at least a portion of the shifted syngas in a carbon dioxide recovery unit to produce recycle carbon dioxide and a hydrogen-enriched syngas, wherein the carbon dioxide recovery unit is a new carbon dioxide recovery unit, an existing carbon dioxide recovery unit, or combinations thereof, (d) recycling at least a portion of the recycle carbon dioxide to the reformer, (e) introducing a portion of the unshifted syngas to a Fischer-Tropsch (FT) unit to produce an FT product, FT water, and FT tail gas, wherein the FT product comprises FT liquids and FT wax, and (f) separating at least a portion of the FT liquids from at least a portion of the FT product to produce a fuel.

Further disclosed herein is a method of producing fuel from carbon dioxide comprising (a) introducing natural gas, steam, and recovered carbon dioxide to a reformer to produce unshifted synthesis gas (syngas), wherein at least a portion of the recovered carbon dioxide is converted to carbon monoxide, and wherein the unshifted syngas is characterized by a molar ratio of hydrogen to carbon monoxide of from about 1.7:1 to about 2.5:1, (b) introducing a portion of the unshifted syngas to a Fischer-Tropsch (FT) unit to produce an FT product, FT water, and FT tail gas, wherein the FT product comprises FT liquids and FT wax, (c) separating at least a portion of the FT liquids from at least a portion of the FT product to produce a fuel, and (d) generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is from about 10% to about 90%.

Also disclosed herein is a method of producing fuel from carbon dioxide comprising (a) introducing natural gas, steam, and recovered carbon dioxide to a reformer to produce unshifted synthesis gas (syngas), wherein at least a portion of the recovered carbon dioxide is converted to carbon monoxide, and wherein the unshifted syngas is characterized by a molar ratio of hydrogen to carbon monoxide of from about 1.7:1 to about 2.5:1, (b) introducing a first portion of the unshifted syngas to a water gas shift unit to produce a shifted syngas, wherein a molar ratio of hydrogen to carbon monoxide in the shifted syngas is greater than a molar ratio of hydrogen to carbon monoxide in the unshifted syngas, and wherein an amount of carbon dioxide in the shifted syngas is greater than an amount of carbon dioxide in the unshifted syngas, (c) separating at least a portion of the carbon dioxide from at least a portion of the shifted syngas to produce recycle carbon dioxide and a hydrogen-enriched syngas, (d) recycling at least a portion of the recycle carbon dioxide to the reformer, (e) introducing a second portion of the unshifted syngas to a Fischer-Tropsch (FT) unit to produce an FT product, FT water, and FT tail gas, wherein the FT product comprises FT liquids and FT wax, (f) separating at least a portion of the FT liquids from at least a portion of the FT product to produce a fuel, and (g) generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is at least 10%.

BRIEF DESCRIPTION OF THE DRAWINGS

For a detailed description of the preferred embodiments of the disclosed methods, reference will now be made to the accompanying drawing in which:

The FIGURE displays a schematic of a process for producing fuels by using recovered carbon dioxide.

DETAILED DESCRIPTION

Figure 1:
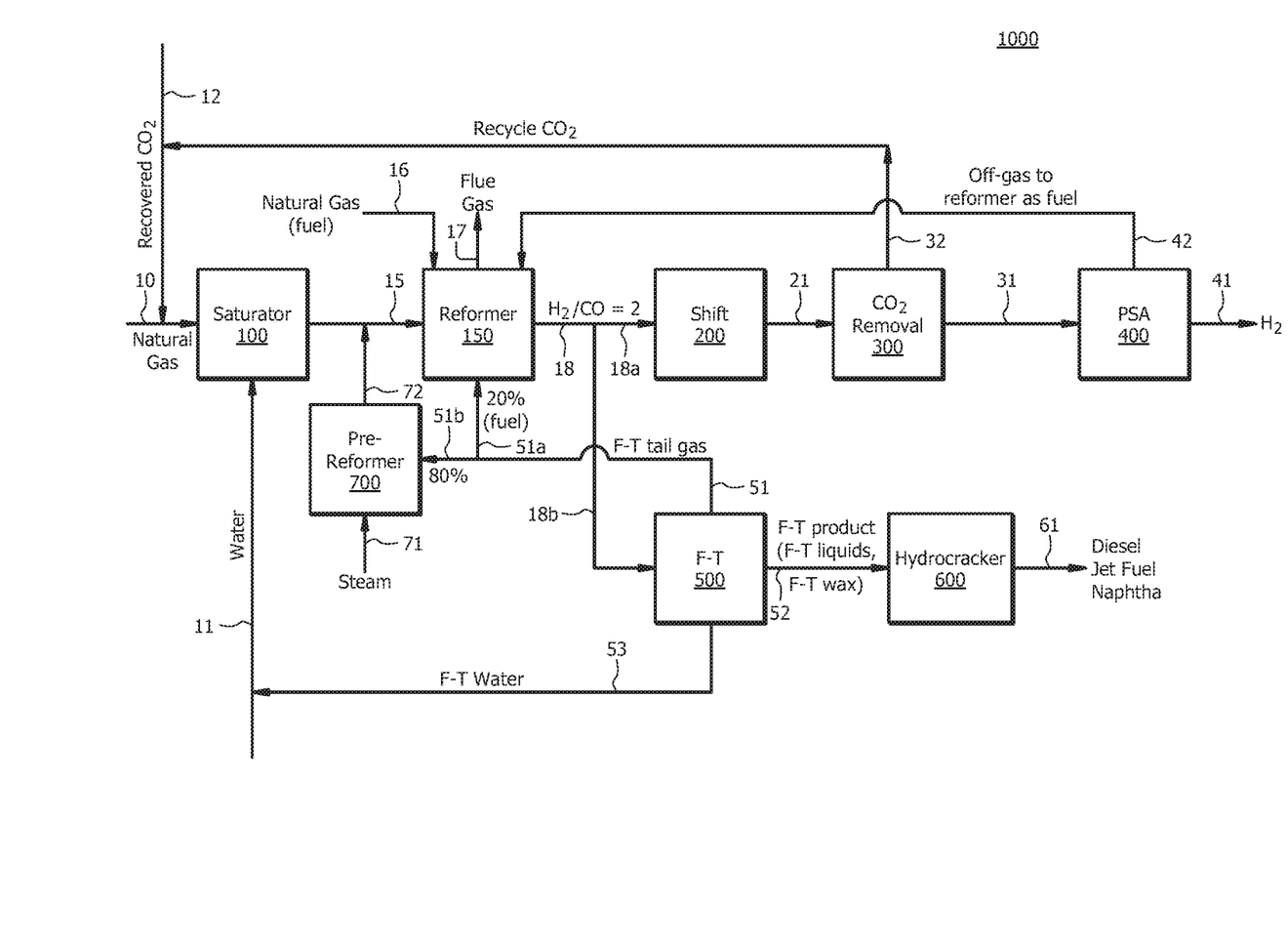

Disclosed herein are methods of producing fuel from carbon dioxide comprising (a) introducing natural gas, steam, and recovered carbon dioxide to a reformer to produce unshifted synthesis gas (syngas), wherein the natural gas comprises primarily methane (CH), wherein the unshifted syngas comprises carbon monoxide (CO), hydrogen ($H_2$), and carbon dioxide ($CO_2$), and wherein the unshifted syngas is characterized by a molar ratio of hydrogen to carbon monoxide of from about 1.7:1 to about 2.5:1; (b) introducing a portion of the unshifted syngas into a water gas shift unit to produce a shifted syngas, wherein the shifted syngas comprises carbon monoxide, hydrogen, and carbon dioxide, wherein a molar ratio of hydrogen to carbon monoxide in the shifted syngas is greater than a molar ratio of hydrogen to carbon monoxide in the unshifted syngas, and wherein an amount of carbon dioxide in the shifted syngas is greater than an amount of carbon dioxide in the unshifted syngas; (c) separating at least a portion of the carbon dioxide from at least a portion of the shifted syngas to produce recycle carbon dioxide and a hydrogen-enriched syngas; (d) recycling at least a portion of the recycle carbon dioxide to the reformer; (e) introducing a portion of the unshifted syngas to a Fischer-Tropsch (FT) unit to produce an FT product, FT water, and FT tail gas, wherein the FT product comprises FT liquids and FT wax; and (f) separating at least a portion of the FT liquids from at least a portion of the FT product to produce a fuel. In an embodiment, the recovered carbon dioxide can comprise at least a portion of the recycle carbon dioxide. In an embodiment, the recovered carbon dioxide can comprise carbon dioxide recovered from a flue gas, a reformer flue gas, a shifted syngas, a carbon dioxide pipeline, associated gas from oil fields, an exhaust gas from fuel combustion in an industrial combustion device, unit, or system (e.g., a burner, furnace, gas-fired turbine, etc.); a refinery vent stream, a natural gas, or combinations thereof.

Also disclosed herein, a method of making a fuel from carbon dioxide may further comprise generating a carbon credit. Further to one or more of the steps described above with respect to the embodiments of a method of making a fuel, generating a carbon credit may comprise a step of (g) quantifying a reduction in emissions of carbon dioxide or a greenhouse gas (GHG) having a carbon dioxide equivalency and a step of (h) claiming a carbon credit associated with the reduction in emissions of carbon dioxide or the GHG having the carbon dioxide equivalency.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosure and does not pose a limitation on the scope of the disclosed subject matter otherwise claimed. No language in the specification should be construed as indicating any non-claimed element essential to the practice of the disclosed subject matter.

Groupings of alternative elements or embodiments disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified.

As used herein, the terms "comprise," "comprises," "comprising," or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures preceded by "comprises [ . . . ] a" does not, without more constraints, preclude the existence of other devices or other sub-systems or other elements or other structures or additional devices or additional sub-systems or additional elements or additional structures.

Reference throughout this specification to "one embodiment," "an embodiment," or similar language means that a particular feature, structure, or characteristic described in connection with the embodiment is included in at least one embodiment of the present disclosure. Thus, appearances of the phrase "in one embodiment," "in an embodiment," and similar language throughout this detailed description may, but do not necessarily, all refer to the same embodiment.

The following discussion provides many exemplary embodiments of the disclosed subject matter. Although each embodiment may represent a single combination of disclosed elements, the disclosed subject matter is considered to include all possible combinations of the disclosed elements. Thus, if one embodiment comprises elements A, B, and C, and a second embodiment comprises elements B and D, then the disclosed subject matter is also considered to include other remaining combinations of A, B, C, or D, even if not explicitly disclosed.

In an embodiment, a method of producing fuel from carbon dioxide can comprise introducing natural gas (e.g., purified natural gas), steam, and recovered carbon dioxide to a reformer or reforming unit to produce unshifted synthesis gas (syngas) that is rich in carbon monoxide (e.g., unshifted CO rich syngas), wherein the unshifted syngas can comprise carbon monoxide and hydrogen.

In an embodiment, the natural gas can comprise methane, carbon dioxide, and contaminants such as sulfur-containing compounds and chlorides. In an embodiment, the natural gas can further comprise hydrocarbons other than methane, such as ethane, propane, butane and pentanes; as well as water vapor and nitrogen. In an embodiment, the sulfur-containing compounds of the natural gas can comprise hydrogen sulfide, carbon sulfide, carbonyl sulfide, carbon disulfide, organic sulfur compounds, and the like, or combinations thereof. In an embodiment, the sulfur-containing compounds of the natural gas can comprise hydrogen sulfide.

In some embodiments, a method of producing fuel from carbon dioxide can further comprise introducing the natural gas to a sulfur removal unit to produce a purified natural gas. In other embodiments, a method of producing fuel from carbon dioxide can further comprise introducing the unshifted syngas to a sulfur removal unit to produce a purified unshifted syngas, as will be discussed in more detail later herein. In an embodiment, the sulfur removal unit can be a sulfur guard bed, wherein the sulfur guard bed can remove traces of sulfur-containing compounds from the natural gas.

In some embodiments, the sulfur removal unit can comprise a fixed bed, wherein the fixed bed comprises mixed metal oxides, such as for example zinc oxides (ZnO), copper oxides (CuO, $Cu_2O$), nickel oxide (NiO), iron oxides (FeO), manganese oxides (MnO, $MnO_2$), a cobalt oxide-molybdenum oxide catalyst, a cobalt-molybdenum-based catalyst, and the like, or combinations thereof, wherein the mixed metal oxides can be unsupported or supported on supports such as alumina, silica, and the like, or combinations thereof. In an embodiment, the sulfur removal unit can comprise a PURASPEC fixed bed, which is commercially available from Johnson Matthey Process Technologies.

In an embodiment, the purified natural gas can comprise sulfur in an amount of less than about 1 part per million volume (ppmv), alternatively less than about 0.5 ppmv, or alternatively less than about 0.1 ppmv. In an embodiment, the purified natural gas is substantially sulfur-free, alternatively sulfur-free. As will be appreciated by one of skill in the art, and with the help of this disclosure, sulfur above certain levels in the natural gas resulting in sulfur above certain levels in the syngas (e.g., unshifted syngas) could poison a catalyst in a Fischer-Tropsch (FT) unit, and such levels are dependent on the type of catalyst used in the FT unit, the type of FT unit, process conditions for the FT unit, etc. When there is sulfur present in the natural gas, such sulfur will be present in the syngas (e.g., unshifted syngas) upon reforming the natural gas, and could poison a catalyst in the FT unit.

Generally, in conventional reforming processes, at least a portion of the sulfur-containing compounds can be separated (e.g., removed) from a feedstock introduced to a reforming unit, as the sulfur-containing compounds could poison the catalyst in the reforming unit. In embodiments where the reformer comprises a sulfur passivated nickel-based catalyst, a natural gas feed to the reformer can be purified to remove sulfur, but it is not necessary. In an embodiment, the natural gas feed to the reforming unit can be considered a sour gas (e.g., sour natural gas) based upon the presence of acid gases such as hydrogen sulfide, carbon dioxide, etc. In an embodiment, the natural gas feed to the reforming unit can comprise hydrogen sulfide in an amount ranging from about 5 ppmv to about 50 ppmv.

In various embodiments, steam can be introduced into the reformer as a component of a natural gas feed stream (e.g., wet gas), as a component of an effluent stream from a pre-reforming unit (e.g., pre-reformer), as a separate steam feed stream, or combinations thereof. In an embodiment, a molar ratio of steam to methane in the total feed streams to the reformer can be from about 0.5:1 to about 4.0:1, alternatively from about 0.75:1 to about 3.0:1, or alternatively from about 0.8:1 to about 2.5:1. In an embodiment, a molar ratio of steam to methane in the total feed streams to the reformer can be from about 0.5:1 to about 1.0:1, alternatively from about 0.6:1 to about 0.9:1, or alternatively from about 0.65:1 to about 0.85:1, for a sulfur passivated nickel-based catalyst. In an embodiment, a molar ratio of steam to methane in the total feed streams to the reformer can be from about 2.5:1 to about 4.0:1, alternatively from about 2.75:1 to about 3.75:1, or alternatively from about 3.0:1 to about 3.5:1, for a sulfur sensitive nickel-based catalyst. Methane can be reformed (e.g., converted to syngas or unshifted syngas) in the presence of water (e.g., steam) according to the general reaction $CH_4 + H_2O \rightleftharpoons CO + 3H_2$. Conventional steam methane reformers use a steam to methane molar ratio of from about 2.5:1 to about 4.0:1, resulting in a syngas with a molar ratio of hydrogen to carbon monoxide of about 3:1, or higher. In an embodiment, the reforming unit as disclosed herein can employ a low steam to methane ratio (when compared to conventional steam reforming processes), in order to produce a syngas (e.g., unshifted syngas) having a molar ratio of hydrogen to carbon monoxide of about 2:1. In some embodiments, steam to the reformer can be provided in the form of FT water after moisturization of natural gas, such as for example in a saturator.

In some embodiments, at least a portion of the natural gas can be contacted with steam and/or water to produce a water saturated natural gas, wherein at least a portion of the water saturated natural gas can be introduced to the reformer. In an embodiment, at least a portion of the natural gas can be contacted with steam and/or water in a saturator (e.g., saturating unit) prior to introducing the natural gas to the reformer, for example by using water produced in an FT unit (e.g., FT water) located downstream of the reformer. The saturator can generally comprise a fixed bed comprising any suitable packing material, wherein the natural gas can contact the water and/or steam inside the fixed bed to produce a water saturated natural gas.

In various embodiments, carbon dioxide can be introduced into the reformer as a component of the natural gas feed stream (e.g., an acid or sour gas), as a component of an effluent stream from the pre-reforming unit, as a separate carbon dioxide feed stream (e.g., recovered carbon dioxide), or combinations thereof. In an embodiment, a molar ratio of carbon dioxide to methane in the total feed streams to the reformer can be from about 0.5:1 to about 1.5:1, alternatively from about 0.5:1 to about 1.0:1, or alternatively from about 1.0:1 to about 1.5:1. In an embodiment, a method of producing fuel from carbon dioxide avoids separating the carbon dioxide from the natural gas prior to introducing the natural gas to the reforming unit. In an embodiment, a method of producing fuel from carbon dioxide excludes separating at least a portion of the carbon dioxide from the natural gas prior to introducing the natural gas to the reforming unit. Generally, in conventional reforming processes, at least a portion of the carbon dioxide can be separated (e.g., removed) from a feedstock introduced to a reforming unit, as the carbon dioxide lowers the molar ratio of hydrogen to carbon monoxide. Carbon dioxide can be converted to carbon monoxide in the presence of hydrogen, according to the general reaction $CO_2+H_2 \rightleftharpoons CO+H_2O$. In an embodiment, the reforming unit as disclosed herein can employ carbon dioxide as part of a feedstock introduced to a reforming unit (when compared to conventional steam reforming processes), in order to produce a syngas (e.g., unshifted syngas) having a molar ratio of hydrogen to carbon monoxide of about 2:1. Converting carbon dioxide to carbon monoxide lowers the molar ratio of hydrogen to carbon monoxide both by consuming hydrogen and producing carbon monoxide. Further, the presence of carbon dioxide can lead to an additional methane reforming reaction as represented by the general reaction $CH_4+CO_2 \rightleftharpoons CO+2H_2$, which in turn can lower the molar ratio of hydrogen to carbon monoxide in the syngas (e.g., unshifted syngas) by producing hydrogen and carbon monoxide in equimolar amounts.

In an embodiment, the reformer can comprise any suitable reactor, such as for example a tubular reactor, a multitubular reactor, and the like, or combinations thereof. In an embodiment, the reformer can comprise a MIDREX reformer, which is commercially available from Midrex Technologies, Inc. In an embodiment, the reformer can comprise an existing reformer in a refinery, such as for example a reformer used for the production of $H_2$; a new reformer, such as for example a new reformer comprising a sulfur passivated nickel-based catalyst; or combinations thereof. For purposes of the disclosure herein, an "existing" unit or piece of equipment (e.g., existing reformer, existing water gas shift unit, existing pressure swing adsorption (PSA) unit, existing carbon dioxide recovery unit, existing hydrocracker, etc.) refers to an unit that already exists at a certain location where the method of producing fuel from carbon dioxide as disclosed herein is implemented (e.g., carried out), and such existing unit can be used for the method of producing fuel from carbon dioxide as disclosed herein. Further, for purposes of the disclosure herein, a "new" unit or piece of equipment (e.g., new reformer, new water gas shift unit, new PSA unit, new carbon dioxide recovery unit, new hydrocracker, etc.) refers to an unit that is brought at a certain location where the method of producing fuel from carbon dioxide as disclosed herein is implemented (e.g., carried out), and such unit is "new" to that particular location, although the unit might have been previously used at another location, and the new unit can be used for the method of producing fuel from carbon dioxide as disclosed herein.

In an embodiment, the reformer can comprise a nickel-based catalyst (e.g., sulfur sensitive nickel-based catalyst) and/or a sulfur passivated nickel-based catalyst (to avoid carbon depositions). Methane reforming (according to the general reaction $CH_4+H_2O \rightleftharpoons CO+3H_2$) is strongly endothermic, and a reaction rate depends on the temperature, pressure and catalyst type. Methane will undergo the reforming reaction at high temperatures; however, in the presence of a catalyst (e.g., nickel-based catalyst), the temperature at which methane can be reformed can be lowered. In an embodiment, the reformer can comprise one or more catalyst filled tubes (e.g., nickel-based catalyst filled tubes). In an embodiment, methane reforming can take place in catalyst filled tubes (e.g., nickel-based catalyst filled tubes). In such embodiment, the catalyst filled tubes can be heated indirectly, such as for example by burning a fuel inside a reactor (e.g., fire box, furnace, etc.) comprising the catalyst filled tubes (e.g., a tube-filled furnace). In an embodiment, any suitable fuel can be used for heating the reformer. Non-limiting examples of fuels suitable for use in the present disclosure for heating the reformer include natural gas, an FT tail gas, methane, propane, butane, waste gas, and the like, or combinations thereof. In an embodiment, a flue gas can be emitted from the reformer, wherein the flue gas comprises fuel combustion products, such as carbon dioxide and water vapor. In some embodiments, a fuel can be burned at a bottom of the reformer, and a flue gas can be vented or emitted at the top of the reformer, wherein furnace tubes filled with catalyst are dispersed within the furnace vessel between fuel burners and the flue gas vent/outlet. As will be appreciated by one of skill in the art, and with the help of this disclosure, the fuel burning (e.g., burner flames) and the fuel combustion products do not contact directly the natural gas travelling through and reforming within the catalyst filled tubes (e.g., nickel-based catalyst filled tubes), the fuel burns inside the reformer and outside the catalyst filled tubes, and the fuel combustion products travel through the reformer and along an outer surface of the catalyst filled tubes towards an outlet for the flue gas. In some embodiments, at least a portion of the flue gas can be introduced to the reformer as recovered carbon dioxide.

In an embodiment, the natural gas, steam, and carbon dioxide can be introduced to the one or more catalyst filled tubes (e.g., nickel-based catalyst filled tubes), wherein the catalyst filled tubes are indirectly heated by burning a fuel, and as the natural gas, steam and carbon dioxide travel along the catalyst filled tubes, methane can be reformed to produce hydrogen and carbon monoxide, carbon dioxide can be converted to carbon monoxide, and the unshifted syngas comprising hydrogen and carbon monoxide can be collected as it exits the catalyst filled tubes.

In an embodiment, the reformer can be characterized by a reforming temperature of from about 800° C. to about 900° C., alternatively from about 800° C. to about 850° C., or alternatively from about 850° C. to about 900° C. In an embodiment, the reformer can be characterized by a reforming pressure of from about 1 bar to about 30 bars, alternatively from about 20 bars to about 30 bars, alternatively from about 1 bar to about 10 bars, alternatively from about 1.5 bars to about 8 bars, or alternatively from about 2 bars to about 5 bars.

In an embodiment, the unshifted syngas can comprise hydrogen, carbon monoxide, carbon dioxide, methane (e.g., unreacted methane, unreformed methane), optionally sulfur-containing compounds (e.g., hydrogen sulfide, carbon sulfide, carbonyl sulfide, carbon disulfide, organic sulfur compounds, etc.), optionally chlorides, and water.

In some embodiments, the unshifted syngas can be characterized by a molar ratio of hydrogen to carbon monoxide of from about 1.7:1 to about 2.5:1, alternatively from about 1.8:1 to about 2.3:1, or alternatively from about 1.9:1 to about 2.1:1, for example if a reformer comprising a sulfur passivated nickel-based catalyst is used, such as a new reformer. In an embodiment, the unshifted syngas can have a molar ratio of hydrogen to carbon monoxide of about 2:1. In other embodiments, the unshifted syngas can be characterized by a molar ratio of hydrogen to carbon monoxide of from about 3:1 to about 4:1, for example if a reformer comprising a sulfur sensitive nickel-based catalyst is used, such as an existing reformer.

In some embodiments, the unshifted syngas can comprise carbon dioxide in an amount of less than about 20 mole % (mol %), alternatively less than about 10 mol %, or alternatively less than about 5 mol %, for example if a reformer comprising a sulfur passivated nickel-based catalyst is used, such as a new reformer. In other embodiments, the unshifted syngas can comprise carbon dioxide in an amount of less than about 50 mol %, for example if a reformer comprising a sulfur sensitive nickel-based catalyst is used, such as an existing reformer (e.g., conventional reformer).

In an embodiment, the unshifted syngas can comprise methane (e.g., unreacted methane, unreformed methane) in an amount of less than about 5 mol %, alternatively less than about 2.5 mol %, alternatively less than about 2 mol %, or alternatively less than about 1 mol %.

In some embodiments, the unshifted syngas can comprise sulfur-containing compounds in an amount of less than about 100 ppmv, or alternatively less than about 10 ppmv, for example if a reformer comprising a sulfur passivated nickel-based catalyst is used, such as a new reformer. In other embodiments, the unshifted syngas can comprise sulfur-containing compounds in an amount of less than about 1 ppmv, for example if a reformer comprising a sulfur sensitive nickel-based catalyst is used, such as an existing reformer. As will be appreciated by one of skill in the art, and with the help of this disclosure, a portion of syngas contaminants (e.g., sulfur-containing compounds, chlorides, etc.) can be in a gas state in the syngas, and a portion of the contaminants can be dissolved in the water present in the syngas.

In some embodiments, the unshifted syngas can have a pressure of from about 5 pounds per square inch gauge (psig) to about 50 psig, for example if a reformer comprising a sulfur passivated nickel-based catalyst is used, such as a new reformer. In other embodiments, the unshifted syngas can have a pressure of from about 300 psig to about 500 psig, for example if a reformer comprising a sulfur sensitive nickel-based catalyst is used, such as an existing reformer.

In an embodiment, a method of producing fuel from carbon dioxide can further comprise introducing at least a portion of the unshifted syngas to a sulfur removal unit to produce a purified unshifted syngas. In an embodiment, the sulfur removal unit can be a sulfur guard bed as previously described herein, wherein the sulfur guard bed can remove traces of sulfur-containing compounds that can be still present in the unshifted syngas.

In an embodiment, the unshifted syngas (e.g., purified unshifted syngas) can comprise sulfur in an amount of less than about 0.1 ppmv, alternatively less than about 0.01 ppmv, or alternatively less than about 0.001 ppmv. In an embodiment, the unshifted syngas (e.g., purified unshifted syngas) is sulfur-free. In an embodiment, the unshifted syngas (e.g., purified unshifted syngas) can be substantially sulfur-free, alternatively sulfur-free. As will be appreciated by one of skill in the art, and with the help of this disclosure, the portion of unshifted syngas that is directed to the shift unit can contain sulfur, while the portion of unshifted syngas that is directed to an FT process has to be sulfur-free (e.g., substantially sulfur-free) to avoid poisoning an FT catalyst.

In an embodiment, a method of producing fuel from carbon dioxide can comprise introducing a portion (e.g., a first portion) of the unshifted syngas to a water gas shift unit (e.g., a shift unit) to produce a shifted syngas, wherein the shifted syngas comprises hydrogen, carbon monoxide, and carbon dioxide. The molar ratio of hydrogen to carbon monoxide in the unshifted syngas can be increased (e.g., adjusted) by introducing the unshifted syngas to a water gas shift unit comprising a sour shift catalyst to convert carbon monoxide and water into additional hydrogen and carbon dioxide according to the general reaction $CO+H_2O \leftrightarrow H_2+CO_2$, also known as the water-gas shift (WGS) reaction. The WGS reaction can be conducted in the presence of a variety of sour shift catalysts at a WGS reaction temperature of from about 400° F. to about 900° F., alternatively from about 450° F. to about 850° F., or alternatively from about 500° F. to about 800° F. The WGS reaction does not change the total number of moles (e.g., two moles of products are produced from two moles of reactants), and as such an effect of pressure on the WGS reaction is minimal. The equilibrium of the WGS reaction can be shifted towards hydrogen production in the presence of high moisture content. Generally, excess moisture can be present in the unshifted syngas that is recovered from the reformer, and such moisture is usually sufficient to drive the WGS reaction to achieve a desired molar ratio of hydrogen to carbon monoxide. In an embodiment, steam can be further introduced to the water gas shift unit to increase the moisture content.

In some embodiments, the unshifted syngas can be heated to a temperature that is greater than a syngas moisture saturation temperature by from about 20° F. to about 75° F., alternatively from about 25° F. to about 60° F., or alternatively from about 30° F. to about 50° F., prior to introducing the unshifted syngas to the water gas shift unit. As will be appreciated by one of skill in the art, and with the help of this disclosure, if the temperature of the unshifted syngas is too low, the water could condense inside the water gas shift unit and such water condensation could damage a sour shift catalyst. The syngas moisture saturation temperature can be from about 350° F. to about 500° F., depending on the unshifted syngas composition and process conditions for producing the unshifted syngas.

In an embodiment, the water gas shift unit (e.g., shift reactor) can comprise any suitable reactor, such as for example a fixed bed reactor, adiabatic reactor, radial reactor, and the like, or combinations thereof. In an embodiment, a water gas shift reactor can comprise a catalyst bed comprising a sour shift catalyst. In an embodiment, the water gas shift unit can be a multi-stage unit, for example the water gas shift unit can comprise multiple reactors and/or multiple fixed beds. In an embodiment, the water gas shift unit can comprise an existing water gas shift unit (e.g., an existing water gas shift unit in a refinery); a new water gas shift unit; or combinations thereof. In an embodiment, the shift reactor can be an existing unit in a refinery, wherein the existing water gas shift unit can be reused with minimum modifications for the method of producing fuel from carbon dioxide as disclosed herein.

The WGS reaction can be catalyzed by both metals and metal oxides. Non-limiting examples of sour shift catalysts suitable for use in the present disclosure include cobalt, molybdenum, copper, iron, a cobalt-molybdenum catalyst, a chromium promoted iron-based catalyst, a copper promoted iron-based catalyst, a copper-zinc-aluminum catalyst, copper oxide (CuO), iron oxide ($Fe_2O_3$), oxides thereof, and the like, or combinations thereof.

In an embodiment, a molar ratio of hydrogen to carbon monoxide in the shifted syngas can be greater than a molar ratio of hydrogen to carbon monoxide in the unshifted syngas. In an embodiment, the shifted syngas can be characterized by a molar ratio of hydrogen to carbon monoxide of equal to or greater than about 100:1, alternatively from about 5:1 to about 100:1, alternatively from about 10:1 to about 75:1, or alternatively from about 15:1 to about 40:1. As will be appreciated by one of skill in the art, and with the help of this disclosure, the molar ratio of hydrogen to carbon monoxide depends on shifting (e.g., CO conversion via the WGS reaction) conditions (e.g., type of WGS unit, type of catalyst used in the WGS unit, etc.). Further, as will be appreciated by one of skill in the art, and with the help of this disclosure, full shifting (e.g., almost all CO undergoes the WGS reaction) can lead to hydrogen to carbon monoxide molar ratios of over 10:1 due to very small CO numbers; single stage, mild shifting can lead to hydrogen to carbon monoxide molar ratios of from about 5:1 to about 10:1; a more moderate level of full shift can lead to hydrogen to carbon monoxide molar ratios of about 7:1; and the hydrogen to carbon monoxide molar ratio decreases with catalyst age.

In an embodiment, an amount of carbon dioxide in the shifted syngas can be greater than an amount of carbon dioxide in the unshifted syngas. As will be appreciated by one of skill in the art, and with the help of this disclosure, carbon dioxide is produced in equimolar amounts with hydrogen via the WGS reaction.

In an embodiment, a method of producing fuel from carbon dioxide can comprise separating at least a portion of the carbon dioxide from at least a portion of the shifted syngas to produce recycle carbon dioxide and a hydrogen-enriched syngas. Generally, carbon dioxide recovery from a gaseous mixture (e.g., shifted syngas) can comprise chemical absorption, physical absorptions, membrane separation, adsorption, cryogenic separation, and the like, or combinations thereof.

In an embodiment, at least a portion of the carbon dioxide can be removed (e.g., recovered, separated, etc.) from at least a portion of the shifted syngas by chemical absorption via an absorption system (e.g., carbon dioxide recovery unit) comprising an absorber (e.g., absorption unit) and a desorber (e.g., regeneration unit or desorption unit), to produce a recycle carbon dioxide. Absorption processes utilize a reversible chemical reaction of carbon dioxide with an aqueous alkaline solvent (e.g., absorber solvent), usually an amine. In the desorber, the absorbed carbon dioxide can be stripped from the solution and recovered, while a regenerated solvent can be sent back to the absorber. Heat is usually provided in a reboiler in the regeneration unit to provide a necessary heat of desorption for carbon dioxide stripping from the solvent. In an embodiment, the carbon dioxide recovery unit can comprise a Fluor Solvent system comprising or consisting of a propylene carbonate solvent, available from Fluor.

In an embodiment, the absorption system can comprise an absorption unit and a solvent regeneration unit, wherein the absorption unit comprises an absorber solvent, such as for example an amine. In an embodiment, the absorber solvent can comprise ammonia, primary amines, secondary amines, tertiary amines, sterically hindered amines, methylethylamine (MEA), methyl diethanolamine (MDEA), diglycolamine (DGA), 2-amino-2-methyl-1-propanol (AMP), dimethyl ethers of polyethylene glycol; and the like; blends thereof; or combinations thereof. In an embodiment, the absorber solvent can be regenerable, e.g., the absorber solvent can be regenerated in the regeneration unit. Generally, the absorber solvent absorbs gas molecules such as carbon dioxide by reacting reversibly with such gas molecules to produce a rich solvent, for example in the absorption unit; and the rich solvent can subsequently undergo the reverse chemical reaction that releases the absorbed gases and regenerates the absorber solvent, for example in the solvent regeneration unit. For purposes of the disclosure herein, the term "absorber solvent" refers to a solvent that preferentially reacts with and consequently absorbs carbon dioxide.

In an embodiment, at least a portion of the shifted syngas and an absorber solvent can be introduced to an absorption unit to produce a hydrogen-enriched syngas and a rich solvent, wherein the rich solvent comprises at least a portion of the carbon dioxide of the shifted syngas, and wherein the hydrogen-enriched syngas comprises at least a portion of the hydrogen of the shifted syngas. In an embodiment, the absorption unit can comprise any suitable absorber column, wherein a gas phase (e.g., shifted syngas) interacts with a liquid phase (e.g., absorber solvent) via co-current flow, counter-flow (e.g., countercurrent), or cross-flow. Generally, absorption columns can be vertical and cylindrical columns or towers. In an embodiment, the absorption unit can comprise a countercurrent absorber column, wherein the shifted syngas can be introduced to the column countercurrent (e.g., opposing flow directions) to the flow of absorber solvent. In such embodiment, the shifted syngas can be in a gas state and the absorber solvent can be in a liquid state, such that the absorption occurs by gas-liquid contacting. In an embodiment, the absorber solvent can be introduced as a downflow at the top of the absorber unit, and the shifted syngas can be introduced (e.g., bubbled) at the bottom of the absorber unit. In such embodiment, the hydrogen-enriched syngas can be recovered at the top of the absorber unit, and the rich solvent can be recovered at the bottom of the absorber unit. The absorber unit can employ an absorber column typically comprising one or more trays and/or packing as a contacting device. However, any other suitable contacting devices can be employed, such as for example static or dynamic mixers, spargers, impellers, etc. In some embodiments, the absorption unit can comprise a packed bed column, a tray column, a spray column, a falling film column, a bubble column, a sparged tank column, and the like, or combinations thereof.

In an embodiment, the hydrogen-enriched syngas can comprise substantially all of the hydrogen present in the shifted syngas. In an embodiment, the hydrogen-enriched syngas can contain equal to or greater than about 50%, alternatively equal to or greater than about 60%, alternatively equal to or greater than about 70%, alternatively equal to or greater than about 80%, alternatively equal to or greater than about 90%, alternatively equal to or greater than about 95%, or alternatively equal to or greater than about 99% of the hydrogen of the shifted syngas.

In an embodiment, the rich solvent can comprise carbon dioxide in an amount of equal to or greater than about 30%, alternatively equal to or greater than about 40%, or alternatively equal to or greater than about 50% of the carbon dioxide of the shifted syngas.

In an embodiment, at least a portion of the rich solvent can be introduced to the solvent regeneration unit to produce the recycle carbon dioxide, and the absorber solvent. Generally, the solvent regeneration unit can be similar to the absorber unit, but operating at different parameters (e.g., pressure, temperature, etc.). A pressure in the solvent regeneration unit can be lower than a pressure in the absorber unit to enable the rich solvent to release gases (e.g., carbon dioxide). A temperature in the solvent regeneration unit can be higher than a temperature in the absorber unit to enable the rich solvent to release gases (e.g., carbon dioxide). As will be appreciated by one of skill in the art, and with the help of this disclosure, a lower pressure and a higher temperature in the solvent regeneration unit can promote or enable a reverse reaction where the absorber solvent releases the gases it had reacted with (e.g., sequestered) in the absorber unit.

In an embodiment, the solvent regeneration unit can comprise any suitable desorption column (e.g., solvent regeneration column), wherein a gas or vapor phase (e.g., absorber solvent vapor, steam, etc.) interacts with a liquid phase (e.g., rich solvent) via co-current flow, counter-flow (e.g., countercurrent), or cross-flow. Generally, desorption columns can be vertical and cylindrical columns or towers. In an embodiment, the solvent regeneration unit can comprise a countercurrent desorption column, wherein a portion of regenerated absorber solvent vapors can be introduced to the column countercurrent (e.g., opposing flow directions) to the flow of rich solvent. In an embodiment, the rich solvent can be introduced as a downflow at the top of the solvent regeneration unit, and a portion of the regenerated absorber solvent can be re-introduced at the bottom (e.g., bubbled) of the solvent regeneration unit as vapor. In such embodiment, carbon dioxide can be recovered at the top of the solvent regeneration unit as recycle carbon dioxide, and the absorber solvent (e.g., regenerated absorber solvent) can be recovered at the bottom of the solvent regeneration unit. An overhead gas stream recovered at the top of the solvent regeneration unit can comprise carbon dioxide and absorber solvent vapors, and can be sent through a condenser to condense the absorber solvent, wherein the condensed absorber solvent can be returned to the top of the solvent regeneration unit. A portion of the absorber solvent recovered at the bottom of the solvent regeneration unit can be sent to a reboiler to produce absorber solvent vapors that can then be introduced (e.g., bubbled) to the bottom of the solvent regeneration unit. Generally, the reboiler can be heated with steam (e.g., low pressure steam at a pressure of from about 400 kPa to about 1,500 kPa), wherein the steam can be recovered from the reboiler as an aqueous condensate, and wherein the recovered aqueous condensate can be further converted into the steam used for heating the reboiler. The remainder of the absorber solvent recovered at the bottom of the solvent regeneration unit can be recycled back to the absorber unit. In some embodiments, the solvent regeneration unit can comprise a packed bed column, a tray column, a spray column, a falling film column, a bubble column, a sparged tank column, and the like, or combinations thereof. In an embodiment, the carbon dioxide recovery unit can comprise an existing carbon dioxide recovery unit in a refinery, such as for example a carbon dioxide recovery in a hydrogen plant in a refinery; a new carbon dioxide recovery unit; or combinations thereof.

In an embodiment, a method of producing fuel from carbon dioxide can comprise recycling at least a portion of the recycle carbon dioxide to the reformer. In an embodiment, the recycle carbon dioxide can comprise substantially all of the carbon dioxide of the shifted syngas. In some embodiments, the recycle carbon dioxide can comprise equal to or greater than about 99%, alternatively equal to or greater than about 99.5%, alternatively equal to or greater than about 99.9%, or alternatively equal to or greater than about 99.99% of the carbon dioxide of the shifted syngas.

In an embodiment, the recovered carbon dioxide can comprise at least a portion of the recycle carbon dioxide. In an embodiment, the recovered carbon dioxide can comprise carbon dioxide recovered from a flue gas, a reformer flue gas, a shifted syngas, a carbon dioxide pipeline, associated gas from oil fields, an exhaust gas from fuel combustion in an industrial combustion device, unit, or system (e.g., a burner, furnace, gas-fired turbine, etc.); a refinery vent stream, a natural gas, or combinations thereof. In an embodiment, the recovered carbon dioxide can comprise carbon dioxide recovered from a reformer flue gas using an amine solvent absorption and stripping system, such as for example ECONAMINE FG TECHNOLOGY and/or ECONAMINE FG PLUS TECHNOLOGY, which are enhanced amine-based $CO_2$ capture processes, and are commercially available from Fluor.

In an embodiment, a method of producing fuel from carbon dioxide can further comprise introducing at least a portion of the hydrogen-enriched syngas to a pressure swing adsorption (PSA) unit to produce hydrogen and a PSA off-gas, wherein the PSA off-gas can comprise unreacted methane (e.g., unreformed methane), residual carbon dioxide (e.g., carbon dioxide that was not removed in the absorption system), and optionally residual hydrogen.

In an embodiment, the hydrogen-enriched syngas can be further cooled, if necessary, to achieve a temperature suitable for introducing to the PSA unit, in a heat exchanger, such as for example in an air or liquid (e.g., water) cooled heat exchanger.

In an embodiment, the PSA unit comprises an adsorbent material. PSA is generally based on physical binding of gas molecules (e.g., hydrogen, methane, carbon dioxide, etc.) to an adsorbent material. Binding strength between the gas molecules and the adsorbent material depends on the gas components, type of adsorbent material, partial pressures of the gas components and operating temperature. Purifying a gas by PSA separation is based on differences in binding strength of the gas components to the adsorbent material. Highly volatile components with low polarity, such as hydrogen, are practically non-adsorbable, as opposed to molecules like methane and carbon dioxide. PSA generally has an adsorption step, and a desorption step. During the adsorption step, high purity hydrogen can be recovered from a PSA unit, as hydrogen will not be adsorbed. Methane and carbon dioxide will be adsorbed by the adsorbent material, and can be recovered during the desorption step.

PSA works at basically constant temperature and uses the effect of alternating pressure and partial pressure to perform the adsorption step and the desorption step. Since heating or cooling is not required, short cycles within the range of minutes can be achieved. A cycle can be defined as the time between the start of two consecutive adsorption steps. The adsorption is carried out at high pressure, until an equilibrium loading is reached, wherein no further adsorption capacity is available and the adsorbent material must be regenerated. The regeneration step can be done by lowering the pressure to slightly above atmospheric pressure resulting in a respective decrease in equilibrium loading. As a result, the gases (e.g., methane, carbon dioxide) that were adsorbed by the adsorbent material are desorbed and the adsorbent material is regenerated. Once the regeneration step is completed, the pressure is increased back to adsorption pressure level and another adsorption step begins. Generally, PSA also involves a purge step between the desorption step and the adsorption step, to ensure that the adsorber material is ready to undergo the next adsorption step.

Non-limiting examples of adsorbent materials suitable for use in the present disclosure include molecular sieves, zeolites, such as 5A zeolite and 13X zeolite, and the like, or combinations thereof.

In an embodiment, the hydrogen-enriched syngas can be introduced to the PSA unit at the bottom, and can travel upwards through the adsorbent material, wherein hydrogen can be recovered at a top of the PSA unit during the adsorption step. In such embodiment, the PSA off-gas comprising methane and carbon dioxide can be recovered at the bottom of the PSA unit during the desorption step.

In an embodiment, the PSA unit comprises from about 2 to about 10 PSA units, alternatively from about 3 to about 8 PSA units, alternatively from about 3 to about 6 PSA units operating in parallel, to provide a continuous supply of hydrogen, and to provide for a continuous uptake of hydrogen-enriched syngas. Once an adsorption step is completed in a PSA unit, and such unit starts a desorption step, another PSA unit can take over the adsorption step to ensure a continuous process. As will be appreciated by one of skill in the art, and with the help of this disclosure, more than one PSA unit can undergo the adsorption step at the same time, and similarly, more than one PSA unit can undergo the desorption step at the same time. As long as there is always a PSA unit undergoing an adsorption step and/or ready to undergo an adsorption step, hydrogen production can be continuous.

In an embodiment, the hydrogen can be characterized by a purity of equal to or greater than about 99%, alternatively equal to or greater than about 99.9%, or alternatively equal to or greater than about 99.99%.

In an embodiment, the adsorption step can be carried out at a pressure of from about 375 psig to about 575 psig, alternatively from about 400 psig to about 550 psig, or alternatively from about 450 psig to about 500 psig.

In an embodiment, the hydrogen can be characterized by a pressure of from about 375 psig to about 575 psig, alternatively from about 400 psig to about 550 psig, or alternatively from about 450 psig to about 500 psig. As will be appreciated by one of skill in the art, and with the help of this disclosure, the hydrogen can have about the same pressure as the pressure used for the adsorption step.

In an embodiment, the desorption step can be carried out at a pressure of from about 5 psig to about 50 psig, alternatively from about 10 psig to about 45 psig, alternatively from about 20 psig to about 40 psig, alternatively from about 25 psig to about 35 psig, or alternatively from about 25 psig to about 30 psig.

In an embodiment, the PSA off-gas can be characterized by a pressure of from about 5 psig to about 50 psig, alternatively from about 10 psig to about 45 psig, alternatively from about 20 psig to about 40 psig, alternatively from about 25 psig to about 35 psig, or alternatively from about 25 psig to about 30 psig. As will be appreciated by one of skill in the art, and with the help of this disclosure, the PSA off-gas can have about the same pressure as the pressure used for the desorption step.

In an embodiment, the PSA off-gas can further comprise hydrogen (e.g., residual hydrogen). Residual hydrogen in the PSA off-gas can usually come from hydrogen that remains in the PSA unit once the adsorption step is finished, and such residual hydrogen is recovered in the PSA off-gas during the desorption step.

In an embodiment, at least a portion of the PSA off-gas can be used as fuel for heating the reformer. In an embodiment, at least a portion of the PSA off-gas can be combined with the fuel used for heating the reformer. The methane and residual hydrogen from the PSA off-gas can combust in the reformer to provide for heating the reformer, and the flue gas can comprise water vapor from such combustion.

In an embodiment, the PSA unit can comprise an existing PSA unit in a refinery, such as for example a PSA in a hydrogen plant in a refinery; a new PSA unit; or combinations thereof.

In an embodiment, a method of producing fuel from carbon dioxide can comprise introducing a portion (e.g., a second portion) of the unshifted syngas to an FT unit to produce an FT product comprising FT liquids and FT wax; FT water; and FT tail gas.

In an embodiment, the unshifted syngas (e.g., purified unshifted syngas) can be converted to liquid hydrocarbons (e.g., FT hydrocarbon liquids) via an FT process. The FT process is generally based on a catalytic chemical reaction in which carbon monoxide and hydrogen in the syngas are converted into hydrocarbons of various molecular weights according to the general reaction $(2n+1) H_2 + n\ CO \rightarrow C_n H_{2n+2} + n\ H_2O$ (e.g., FT reaction), wherein n is an integer. There are other side reactions taking place in the FT process, among which the water-gas shift (WGS) reaction $CO + H_2O \leftrightarrow H_2 + CO_2$ is predominant. FT process conditions can be selected to achieve a desired hydrocarbon product distribution. Depending on catalyst, temperature, and type of process employed, an FT process can produce a mixture of hydrocarbons ranging from methane to higher molecular weight paraffins, aromatic hydrocarbons, and olefins; as well as small amounts of low molecular weight oxygenates (e.g., alcohol and organic acids). Waxes (e.g., FT waxes comprising longer-chain paraffins with 20 to 40 carbon molecules that are solid at standard conditions) can also be formed in an FT process; however, such waxes can be cracked to shorter, liquid forms inside a hydrocracker.

In an embodiment, the FT product comprises tail gas (e.g., FT tail gas), unconverted syngas, distillate, light hydrocarbons, naphtha, jet fuel, diesel and wax (e.g., FT wax). In an embodiment, the FT product comprises FT wax in an amount of less than about 50 weight % (wt. %), alternatively less than about 40 wt. %, or alternatively less than about 30 wt %, with the balance of the FT product being non-waxy liquid hydrocarbons (e.g., FT hydrocarbon liquids).

In an embodiment, the FT unit can comprise any suitable FT reactor, such as for example a tubular reactor, a multitubular reactor, a fixed bed reactor, a multitubular fixed-bed reactor, a fluidized bed reactor, a slurry reactor, a microchannel reactor, and the like, or combinations thereof. The FT reaction is highly exothermic, therefore efficient heat removal is an important feature of the FT unit (e.g., FT reactor). In an embodiment, the FT unit (e.g., FT reactor) can comprise an FT catalyst, wherein the FT catalyst can comprise transition metals, such as iron, cobalt, nickel, ruthenium, etc. The FT process is exothermic, and the FT reaction temperature can be generally controlled by cooling the reactor to achieve the desired FT reaction temperature, for example by using a cooling liquid such as water. In an embodiment, the FT reactor can be a tubular reactor, a microchannel reactor, or combinations thereof, wherein the FT reactor comprises a catalyst comprising iron and/or cobalt.

In an embodiment, the FT product can be separated into fractions (e.g., a liquid hydrocarbon fraction and a wax fraction). In an embodiment, at least a portion of the FT liquids can be separated from at least a portion of the FT product to produce a fuel, for example via distillation. In an embodiment, the fuel can comprise diesel fuel, jet fuel, gasoline, and the like, or combinations thereof. The FT liquids can be collected as different fractions, such as jet fuel, diesel fuel, gasoline, naphtha fraction, etc. The naphtha fraction can be introduced to a naphtha reformer to produce a high-octane fuel and hydrogen.

In some embodiments, a heavy FT oil comprising FT wax can be routed to an existing hydrocracker in a refinery to avoid installing a new hydrocracking unit.

In an embodiment, an amount of fuel produced can be increased by equal to or greater than about 30%, alternatively by equal to or greater than about 40%, or alternatively by equal to or greater than about 50%, when compared to an amount of fuel produced by an otherwise similar method lacking introducing recovered carbon dioxide to the reformer. In an embodiment, at least a portion of the recovered carbon dioxide that is introduced to the reformer can be converted to the fuel. Carbon dioxide is converted to carbon monoxide in the reformer, as previously described herein, and carbon monoxide (as part of the unshifted syngas) is communicated to the FT unit where it is further converted into the hydrocarbons that form the fuel. Thus, introducing carbon dioxide to the reformer increases the amount of fuel produced.

In an embodiment, at least a portion of the FT product and hydrogen can be introduced to a hydrocracker (e.g., hydrocracking unit) to produce a fuel. In some embodiments, the FT wax can be separated and recovered from the FT product, wherein at least a portion of the FT wax can be introduced to a hydrocracker to produce a fuel. In other embodiments, the FT product comprising both the FT liquids and the FT wax can be introduced to a hydrocracker to produce a fuel. In an embodiment, the hydrocracker can comprise an existing hydrocracker in a refinery; a new hydrocracker; or combinations thereof.

Generally, a hydrocracking unit, or hydrocracker, cracks (e.g., hydrocracks) or splits heavy molecules into smaller or lighter molecules in the presence of hydrogen and a catalyst. There are two main chemical reactions occurring in the hydrocracker: (i) catalytic cracking of heavy hydrocarbons into lighter unsaturated hydrocarbons and (ii) saturation of these newly formed hydrocarbons with hydrogen. Catalytic cracking of the heavier hydrocarbons uses heat and causes the feed to be cooled as it progresses through the hydrocracker. The saturation of the lighter hydrocarbons releases heat and causes the feed and products to heat up as they proceed through the hydrocracker. Hydrogen can be used to control the temperature of the hydrocracker, by introducing the hydrogen to the hydrocracker at different points. In an embodiment, at least a portion of the hydrogen recovered from the PSA unit can be introduced to the hydrocracker.

Generally, hydrocracking can be facilitated by a bifunctional catalyst that is capable of rearranging and breaking hydrocarbon chains as well as adding hydrogen to aromatics and olefins to produce naphthenes and alkanes, respectively. In some embodiments, a hydrocracking catalyst can comprise both acidic sites, which provide the cracking function, and metal sites, which provide the hydrogenation-dehydrogenation function. Typical acidic supports for hydrocracking catalysts can be amorphous oxides or mixtures of oxides, zeolites and silicoalumina-phosphates. Pt, Pd, and/or bimetallic systems (e.g., Ni/Mo, Ni/W, Co/Mo, in the sulfided form) are the most commonly used metals for hydrocracking catalysts.

In an embodiment, the FT water can comprise water and hydrocarbons. In an embodiment, the FT water can comprise hydrocarbons in an amount of from about 1 wt. % to about 5 wt. %, alternatively from about 1.5 wt. % to about 4.5 wt. %, or alternatively from about 2 wt. % to about 4 wt. %. Generally, for the FT water to be further used, it would be necessary to remove the hydrocarbons from the water. In an embodiment, a method of producing fuel from carbon dioxide excludes treating the FT water for hydrocarbon removal.

In an embodiment, a portion of the FT water can be introduced to the reforming unit, wherein at least a portion of the hydrocarbons of the FT water can be converted to syngas in the reforming unit. When the FT water is introduced to the reforming unit, the presence of the hydrocarbons in the FT water is acceptable, as the water is used in an environment containing hydrocarbons; the reforming unit also comprises hydrocarbons introduced as part of the natural gas. As will be appreciated by one of skill in the art, and with the help of this disclosure, the hydrocarbons of the FT water can be reformed over a reforming catalyst (e.g., nickel-based catalyst, sulfur passivated nickel-based catalyst, etc.) to produce syngas. In an embodiment, a portion of the FT water can be converted to steam for use in the reformer. In an embodiment, at least a portion of the FT water can be introduced to the saturator to saturate with moisture a natural gas feed into the reformer.

In an embodiment, an FT tail gas can be recovered from the FT unit. In an embodiment, the FT tail gas can comprise olefins, unreacted syngas, and carbon dioxide, wherein the unreacted syngas can comprise carbon monoxide and hydrogen. Fuel gases like methane, propane and butane, can usually be formed in FT synthesis (e.g., in the FT unit), and such gases can be recovered as part of the FT tail gas.

In an embodiment, from about 5 volume % (vol. %) to about 35 vol. %, alternatively from about 10 vol. % to about 30 vol. %, or alternatively from about 15 vol. % to about 25 vol. % of the FT tail gas can be used as fuel for heating the reformer, the pre-reforming unit, and the like, or combinations thereof. In an embodiment, a portion of the FT tail gas can be used as fuel for heating the reformer, the pre-reforming unit, and the like, or combinations thereof. In some embodiments, a portion of the FT tail gas can be combined with the fuel used for heating the reformer, the pre-reforming unit, and the like, or combinations thereof.

In an embodiment, at least a portion of the FT tail gas and steam can be introduced to the pre-reforming unit to produce hydrogenated hydrocarbons, wherein at least a portion of the olefins of the FT tail gas can react with at least a portion of the hydrogen of the FT tail gas to produce the hydrogenated hydrocarbons. In an embodiment, from about 65 vol. % to about 95 vol. %, alternatively from about 70 vol. % to about 90 vol. %, or alternatively from about 75 vol. % to about 85 vol. % of the FT tail gas can be introduced to the pre-reforming unit to produce hydrogenated hydrocarbons. In an embodiment, a portion of the FT water can be converted to steam for use in the pre-reforming unit.

In an embodiment, the pre-reforming unit can comprise any suitable hydrogenation reactor, such as for example a tubular reactor, a multitubular reactor, a flow reactor, a plug flow reactor, and the like, or combinations thereof. In an embodiment, the pre-reforming unit can comprise any suitable hydrogenation catalyst, such as for example a nickel-based catalyst, a palladium-based catalyst, a platinum-based catalyst, and the like, or combinations thereof.

In an embodiment, a method of producing fuel from carbon dioxide can comprise introducing at least a portion of the hydrogenated hydrocarbons to the reformer. In an embodiment, an effluent from the pre-reforming unit can comprise the hydrogenated hydrocarbons, carbon dioxide, carbon monoxide, and any residual unreacted olefins and/or hydrogen. In such embodiment, at least a portion of the effluent from the pre-reforming unit comprising the hydrogenated hydrocarbons can be introduced to the reformer. In an embodiment, at least a portion of the hydrogenated hydrocarbons can be converted to syngas in the reformer. As will be appreciated by one of skill in the art, and with the help of this disclosure, the hydrogenated hydrocarbons recovered from the pre-reforming unit can be reformed over a reforming catalyst (e.g., nickel-based catalyst, sulfur passivated nickel-based catalyst, etc.) to produce syngas. Further, the carbon dioxide of the FT tail gas can be converted to carbon monoxide in the presence of hydrogen in the reformer, as previously described herein.

In some embodiments, at least a portion of the natural gas can be introduced to the pre-reforming unit, along with at least a portion of the FT tail gas, wherein at least a portion of the natural gas and at least a portion of the hydrogenated hydrocarbons produced by hydrogenation of the olefins of the FT tail gas can be communicated from the pre-reforming unit to the reforming unit.

In an embodiment, a method of producing fuel from carbon dioxide can comprise setting up (e.g., assembling) at least one modular system for producing fuel from carbon dioxide at any suitable location where carbon dioxide is produced and can be recovered (e.g., as recovered carbon dioxide), wherein each modular system can comprise a saturating unit, a pre-reforming unit, a reforming unit, a sulfur removal unit, a water gas shift unit, a carbon dioxide recovery unit, a PSA unit, an FT unit and a hydrocracking unit. That is, a given modular system may comprise a plurality of units, e.g., a saturating unit, a pre-reforming unit, a reforming unit, a sulfur removal unit, a water gas shift unit, a carbon dioxide recovery unit, a PSA unit, an FT unit and a hydrocracking unit. Furthermore, a plurality of modular systems may be combined in a spread or array to provide cumulative processing/production capacity over a single modular system.

In an embodiment, setting up at least one modular system for producing fuel from carbon dioxide at a suitable location (carbon dioxide producer location) can comprise transporting each unit of the modular system to the location, wherein each unit can be transported concurrently, sequentially, or combinations thereof, with respect to the other units. Accordingly, each unit will be sized and configured for ease of transport to the location. For example, a unit for service at terrestrial sites may be sized and configured for overland transport (e.g., placed on a trailer or skid) as a standard or oversize tractor-trailer transport. A unit for service at offshore sites may be sized and configured for ship transport (e.g., placed on a barge or skid). Each unit can be optionally stored on location, as necessary. Each unit can be placed or positioned on location in a cooperative structural arrangement or position (including at various elevations, if needed for example to facilitate gravity flow).

In an embodiment, setting up at least one modular system for producing fuel from carbon dioxide can comprise connecting (e.g., providing fluid communication among) each unit of the modular system with any other suitable unit through any suitable conduits (e.g., pipes, streams, etc.), as well as connecting each unit with any necessary inflow streams and/or outflow streams, such as for example, power (electrical, hydraulic, mechanical/shaft-drive, etc.), water, cooling water, steam, fuel, flue gas (e.g., exhaust gas) outlet, natural gas inlet, FT product outlet, etc.

In an embodiment, the at least one modular system comprises a plurality of modular systems forming a spread or array comprising from 1 to about 4, alternatively from 1 to about 3, or alternatively from 1 to about 2 modular systems. As will be appreciated by one of skill in the art, and with the help of this disclosure, any suitable number of modular systems can be used to form a suitable spread or array, and the number of modular systems is dependent on the amount of carbon dioxide that is recovered at a particular location. For example, a spread comprising 4 modular systems could be set up and producing fuel from recovered carbon dioxide at a given carbon dioxide generator location, and later on, if the carbon dioxide production declines (for example because of downsizing a plant that produces a carbon dioxide by-product); 1, 2, or 3 of the modular systems could be disassembled (e.g., taken apart), and 3, 2, or 1 of the modular systems, respectively, could remain assembled and functional, continuing to process the available recovered carbon dioxide, based on the amount of carbon dioxide available for processing at that particular location. Accordingly, if the carbon dioxide production declines over time, fewer modular systems may be employed, with each operating at a higher total throughput and reduced total operating costs to improve overall carbon dioxide conversion to fuel economics. As will be appreciated by one of skill in the art, and with the help of this disclosure, the amount of fuel produced by one modular system is dependent (among other factors) upon the amount of recovered carbon dioxide introduced to that particular modular system. While the current disclosure is discussed in detail in the context of setting up from 1 to about 4 modular systems, it should be understood that any suitable number of modular systems could be set up and employed at a particular location, such as for example one, two, three, four, five, six, seven, eight, nine, ten, or more modular systems could be set up and employed at a particular location.

In an embodiment, disassembling one or more modular systems for producing fuel from carbon dioxide can comprise disconnecting each unit from any other units, for example by disconnecting any suitable conduits (e.g., pipes, streams, etc.), as well as disconnecting each unit from any inflow streams and/or outflow streams, such as for example, water, cooling water, steam, fuel, flue gas (e.g., exhaust gas) outlet, natural gas inlet, FT product outlet, etc.

In an embodiment, individual units of one or more disassembled modular systems can be moved (e.g., transported) to another suitable location for producing fuel from carbon dioxide at the another suitable location site. Each unit can be transported concurrently, sequentially, or combinations thereof, with respect to the other units. Each unit can be optionally stored at the another suitable location, as necessary, and could be placed on its location where it will be operating from. In such embodiment, the one or more disassembled modular systems can be set up at the another suitable location as previously described herein.

In an embodiment, a method of producing a fuel from carbon dioxide can further comprise generating a carbon credit. Further to one or more of the steps described above with respect to the embodiments of a method of producing a fuel, generating a carbon credit may comprise the step of quantifying a reduction in emissions of carbon dioxide or a greenhouse gas (GHG) having a carbon dioxide equivalency and the step of claiming the carbon credit associated with the reduction in emissions of carbon dioxide or the GHG having the carbon dioxide equivalency (e.g., a carbon offset).

Every GHG has a global warming potential ("GWP"), a measurement of the impact that a particular gas has on "radiative forcing;" that is, the additional heat/energy which is retained in the Earth's ecosystem as a result of the addition of this particular gas to the atmosphere. The GWP of a given gas describes its effect on climate change relative to a similar amount of carbon dioxide. As the base unit, carbon dioxide's GWP numerical value is 1.0. This allows regulated GHGs to be converted to the common unit of carbon dioxide equivalents ("$CO_2e$"). For example, methane, a $CO_2e$, has a GWP of 21, meaning that one ton of methane will have an effect on global warming that is 21 times greater than one ton of carbon dioxide.

Carbon trading (e.g., trading carbon credits) is an application of an emissions trading scheme. GHG emissions are capped and then markets are used to allocate the emissions among the group of regulated sources. The goal is to allow market mechanisms to drive industrial and commercial processes in the direction of low emissions or less carbon intensive approaches than those used when there is no cost to emitting carbon dioxide and other GHGs into the atmosphere. Since GHG reduction projects generate credits (e.g., associated with carbon offsets), this approach can be used to finance carbon reduction schemes.

Climate exchanges have been established to provide a spot market in allowances, as well as futures and options market to help discover a market price and maintain liquidity. Currently there are five exchanges (e.g., public exchanges) trading in carbon allowances: the Chicago Climate Exchange, European Climate Exchange, Nord Pool, PowerNext and the European Energy Exchange. Carbon prices are normally quoted in Euros per ton of carbon dioxide or its carbon dioxide equivalent ($CO_2e$). Other GHGs (e.g., methane) can also be traded, but are nonetheless quoted as standard multiples of carbon dioxide with respect to their GWP. These features reduce a GHG cap's financial impact on business, while ensuring that the GHG's limits are met at a national and international level.

As previously disclosed herein, the disclosed methods of producing a fuel from carbon dioxide can result in an overall reduction in the emission of $CO_2$ in comparison to an otherwise similar method lacking the steps of introducing recovered carbon dioxide to the reformer. Particularly, and as previously disclosed, in the disclosed methods and systems, $CO_2$ that conventionally (e.g., in an otherwise similar process with the exception that recovered carbon dioxide is not introduced into the reformer) would be vented (e.g., to the atmosphere) is instead recovered (e.g., collected) and advantageously utilized in the disclosed fuel-making processes. More particularly, in an embodiment of the systems and methods disclosed herein, the carbon dioxide stream from the carbon dioxide recovery unit (e.g., recycle carbon dioxide stream 32 from the carbon dioxide recovery unit 300) can be recovered and utilized in the disclosed methods and systems (e.g., reintroduced into the process and/or system); conventionally, the carbon dioxide stream from the carbon dioxide recovery unit would have been vented and, thus would have constituted a carbon dioxide emission. Similarly, in an additional or alternative embodiment of the systems and methods disclosed herein, the flue gas from the reformer (e.g., flue gas stream 17 from reformer 150) can be recovered and at least a portion thereof (e.g., carbon dioxide) may be utilized in the disclosed methods and systems (e.g., reintroduced into the process and/or system); conventionally, the flue gas from the reformer would have been vented and, thus would have constituted a carbon dioxide emission.

In an embodiment, a step of quantifying a reduction in emissions of carbon dioxide or a GHG having a carbon dioxide equivalency generally comprises determining (calculating) a difference between the carbon dioxide that would have been lost (e.g., vented) in a conventional process or system (e.g., a process or system that is otherwise similar to the disclosed processes and systems with the exception that recovered carbon dioxide is not introduced into the reformer) and the carbon dioxide lost in the systems and methods disclosed herein.

In an embodiment, the reduction in carbon dioxide emissions may be calculated on a rate basis. For example, on the basis of the rate at which carbon dioxide emissions are reduced with respect to some process variable, for example, a process input (e.g., the natural gas fed into the saturator or the fuel used to heat the reformer), a process output (e.g., the hydrogen gas yielded by the process, the fuel yielded by the process, etc.), or combinations thereof. The rate at which carbon dioxide emissions are reduced per unit of process variable may be obtained experimentally and/or by calculating the mass of carbon dioxide that would be present based upon a compositional and/or stoichiometric relationship to that process variable. By understanding the rate at which carbon dioxide emissions are reduced per unit of process variable, it is possible to calculate the total reduction in carbon dioxide emissions (e.g., metric tons of carbon dioxide not emitted over a given duration). Alternatively, the reduction in carbon dioxide emissions may be determined by monitoring the mass of particular stream, for example, the recycle carbon dioxide stream that is returned (e.g., recycled) to the reformer.

In an embodiment, a method of producing a fuel from carbon dioxide can further comprise generating at least one carbon credit from a reduction in emissions (e.g., reduction in emissions of carbon dioxide or a GHG having a carbon dioxide equivalency) associated with consumed carbon dioxide of the recovered carbon dioxide fed to the reformer. In an embodiment, the reduction in emissions (e.g., reduction in emissions of carbon dioxide or a GHG having a carbon dioxide equivalency) may be calculated via a mass balance for the recovered carbon dioxide introduced to a fuel production system (such as fuel production system 1000, which will be described in more detail later herein), by accounting for the recovered carbon dioxide that was consumed in the fuel production system. In an embodiment, the reduction in emissions (e.g., reduction in emissions of carbon dioxide or a GHG having a carbon dioxide equivalency) can be a mass of carbon dioxide consumed in the recovered carbon dioxide stream fed to the reformer, wherein the mass of consumed carbon dioxide refers to the mass of recovered carbon dioxide that was consumed overall in the fuel production system. For example, the reduction in carbon dioxide emissions can be a difference between a total mass or amount of carbon dioxide introduced to a fuel production system (e.g., fed to a reformer) as part of the recovered carbon dioxide, and a mass or amount of carbon dioxide that was introduced to the fuel production system as part of the recovered carbon dioxide and was subsequently recovered from the fuel production system, for example in the unshifted syngas, in a flue gas comprising combustion products from burning a portion of the FT tail gas, etc. The reduction in emissions (e.g., reduction in emissions of carbon dioxide or a GHG having a carbon dioxide equivalency) can be expressed as a mass of carbon dioxide or of a GHG having a carbon dioxide equivalency (e.g., mass of carbon dioxide of the recovered carbon dioxide that was consumed in the fuel production system). The reduction in emissions expressed as a mass of carbon dioxide or of a GHG having a carbon dioxide equivalency can be used for generating at least one carbon credit, as a carbon credit generally refers to a tradable certificate, permit, or other negotiable instrument representing the right to emit one ton of carbon dioxide or the mass of another GHG having a carbon dioxide equivalency of one ton of carbon dioxide. A one ton reduction in emissions of carbon dioxide or a reduction in GHG emissions having a carbon dioxide equivalency of one ton of carbon dioxide can be used for generating one carbon credit.

In an embodiment, a % reduction (by weight) in carbon dioxide emissions can be the mass or amount of carbon dioxide that was introduced to the fuel production system as part of the recovered carbon dioxide and was not recovered in any effluents of the fuel production system (e.g., unshifted syngas, combustion products from burning a portion of the FT tail gas, etc.) (×100%); divided by the total mass or amount of carbon dioxide that was introduced to the fuel production system as part of the recovered carbon dioxide. As will be appreciated by one of skill in the art, and with the help of this disclosure, the mass balance across a fuel production system as disclosed herein is complex: a portion of the carbon dioxide introduced to the reformer can be converted to carbon monoxide; however, a portion of this carbon monoxide can be converted back to carbon dioxide in the FT unit (via the WGS reaction), and can be subsequently emitted in the flue gas by burning a portion of the FT tail gas to heat the reformer. If for some reason the carbon dioxide of the flue gas is not recovered and returned to the reformer, any carbon dioxide emitted via the flue gas and originating in the recovered carbon dioxide introduced to the reformer may not be considered as resulting in a reduction in emissions (e.g., reduction in carbon dioxide emissions).

In an embodiment, the systems and methods disclosed herein may achieve a reduction in carbon dioxide emissions of at least 10% by weight (e.g., the mass of carbon dioxide emitted in the disclosed processes and systems is at least 10% less than an otherwise similar process or system with the exception that recovered carbon dioxide is not introduced into the reformer), alternatively, a reduction in carbon dioxide emissions of at least 20%, alternatively, at least 30%, alternatively, at least 40%, alternatively, at least 50%, alternatively, at least 60%, alternatively, at least 70%, alternatively, at least 75%, alternatively, at least 80%, alternatively, at least 85%, alternatively, at least 90%, alternatively, at least 91%, alternatively, at least 92%, alternatively, at least 93%, alternatively, at least 94%, or alternatively, at least 95%.

In an embodiment, the step of claiming the carbon credit associated with the reduction in emissions of carbon dioxide or a GHG having the carbon dioxide equivalency generally comprises requesting that a suitable carbon-credit-awarding entity awards one or more carbon credits on the basis of the reduction in carbon dioxide emissions resulting from the systems and processes disclosed herein. An example of a carbon-credit-awarding entity is the Clean Development Mechanism (CDM), which validates carbon offset projects to ensure they produce actual reductions in carbon dioxide or other GHGs emissions.

In an embodiment, at least a portion of at least one carbon credit can be used as an offset for an industrial gas-producing process. In an embodiment, an entity that obtains a carbon credit, for example, as disclosed herein, may benefit (e.g., economic benefit) from both international and national emissions trading mechanisms monetizing those carbon credits on the appropriate climate exchanges. Such monetization would allow such entities to maximize the economic output of the fuel-making processes and systems disclosed herein.

In an embodiment, a method of producing fuel from carbon dioxide can comprise (a) introducing natural gas, steam, and recovered carbon dioxide to a reformer to produce unshifted synthesis gas (syngas), wherein the unshifted syngas is characterized by a molar ratio of hydrogen to carbon monoxide of from about 1.7:1 to about 2.5:1; (b) introducing a portion of the unshifted syngas to a water gas shift unit to produce a shifted syngas, wherein the shifted syngas comprises carbon monoxide, hydrogen, and carbon dioxide, wherein a molar ratio of hydrogen to carbon monoxide in the shifted syngas is greater than a molar ratio of hydrogen to carbon monoxide in the unshifted syngas, and wherein an amount of carbon dioxide in the shifted syngas is greater than an amount of carbon dioxide in the unshifted syngas; (c) separating at least a portion of the carbon dioxide from a first portion of the shifted syngas to produce recycle carbon dioxide and a hydrogen-enriched syngas; (d) recycling at least a portion of the recycle carbon dioxide to the reformer; (e) introducing a second portion of the unshifted syngas to an FT unit to produce an FT product, FT water, and FT tail gas, wherein the FT product comprises FT liquids and FT wax; (f) separating at least a portion of the FT liquids from at least a portion of the FT product to produce a fuel; (g) introducing at least a portion of the FT product and hydrogen to a hydrocracker to produce a fuel; and (h) generating a carbon credit from a reduction in emissions of carbon dioxide or a GHG having a carbon dioxide equivalency associated with consumed carbon dioxide of the recovered carbon dioxide fed to the reformer, wherein the reduction is at least 10%, alternatively at least 20%, alternatively at least 30%, alternatively at least 40%, alternatively at least 50%, alternatively at least 60%, alternatively at least 70%, alternatively at least 80%, alternatively at least 90%, alternatively from about 10% to about 90%, alternatively from about 15% to about 85%, or alternatively from about 20% to about 80%.

In an embodiment, a method of producing fuel from carbon dioxide can comprise (a) introducing natural gas, steam, and recovered carbon dioxide to a reformer to produce unshifted synthesis gas (syngas), wherein the unshifted syngas comprises carbon monoxide, hydrogen, and carbon dioxide, wherein at least a portion of the recovered carbon dioxide is converted to carbon monoxide, and wherein the unshifted syngas is characterized by a molar ratio of hydrogen to carbon monoxide of from about 1.7:1 to about 2.5:1; (b) introducing a portion of the unshifted syngas to an FT unit to produce an FT product, FT water, and FT tail gas, wherein the FT product comprises FT liquids and FT wax; (c) separating at least a portion of the FT liquids from at least a portion of the FT product to produce a fuel; (d) introducing at least a portion of the FT product and hydrogen to a hydrocracker to produce a fuel; and (e) generating a carbon credit from a reduction in emissions of carbon dioxide or a GHG having a carbon dioxide equivalency associated with consumed carbon dioxide of the recovered carbon dioxide fed to the reformer, wherein the reduction is at least 10%, alternatively at least 20%, alternatively at least 30%, alternatively at least 40%, alternatively at least 50%, alternatively at least 60%, alternatively at least 70%, alternatively at least 80%, alternatively at least 90%, alternatively from about 10% to about 90%, alternatively from about 15% to about 85%, or alternatively from about 20% to about 80%.

Referring to the embodiment of the FIGURE, a fuel production system 1000 is disclosed. The fuel production system 1000 generally comprises a saturator 100 (e.g., new saturator); a reformer 150 (e.g., new reformer; existing reformer, for example in a refinery; or combinations thereof); a water gas shift unit 200 (e.g., new water gas shift unit; existing water gas shift unit, for example in a refinery; or combinations thereof); a carbon dioxide recovery unit 300 (e.g., new carbon dioxide recovery unit; existing carbon dioxide recovery unit, for example in a refinery; or combinations thereof); a PSA unit 400 (e.g., new PSA unit; existing PSA unit, for example in a refinery; or combinations thereof); an FT unit 500 (e.g., new FT unit); a hydrocracker 600 (e.g., new hydrocracker; existing hydrocracker, for example in a refinery; or combinations thereof); and a pre-reforming unit 700 (e.g., new pre-reforming unit). As will be appreciated by one of skill in the art, and with the help of this disclosure, components of the fuel production system can be in fluid communication with each other through any suitable conduits (e.g., pipes, streams, etc.).

In an embodiment, a method of producing fuel from carbon dioxide can comprise one or more of the following: (a) introducing a natural gas stream 10, a recovered carbon dioxide stream 12, and a water stream 11 to the saturator 100 to produce a water saturated natural gas stream 15, wherein the water saturated natural gas comprises natural gas, carbon dioxide, and steam, and wherein the natural gas comprises methane; (b) introducing at least a portion of the water saturated natural gas stream 15 to the reformer 150 to produce an unshifted synthesis gas (syngas) stream 18, wherein at least a portion of the recovered carbon dioxide is converted to carbon monoxide in the reformer, wherein the unshifted syngas comprises hydrogen and carbon monoxide in a molar ratio of from about 1.7:1 to about 2.5:1 (alternatively, the unshifted syngas comprises hydrogen and carbon monoxide in a molar ratio of about 2:1), wherein the reformer 150 comprises a sulfur passivated nickel-based catalyst, wherein a natural gas stream 16 can be used as fuel to heat the reformer 150, wherein a flue gas stream 17 can be emitted from the reformer 150, and wherein the flue gas comprises fuel combustion products; (c) introducing a first unshifted syngas stream 18a to a water gas shift unit 200 to produce a shifted syngas stream 21, wherein the first unshifted syngas stream 18a comprises a portion of the unshifted syngas stream 18, wherein the shifted syngas comprises hydrogen, carbon monoxide, and carbon dioxide, wherein a molar ratio of hydrogen to carbon monoxide in the shifted syngas is greater than a molar ratio of hydrogen to carbon monoxide in the unshifted syngas, and wherein an amount of carbon dioxide in the shifted syngas is greater than an amount of carbon dioxide in the unshifted syngas; (d) introducing at least a portion of the shifted syngas stream 21 to the carbon dioxide recovery unit 300 to produce a recycle carbon dioxide stream 32 and a hydrogen-enriched syngas stream 31; (e) recycling at least a portion of the recycle carbon dioxide stream 32 to the saturator 100 (for example via the recovered carbon dioxide stream 12); (f) introducing at least a portion of the hydrogen-enriched syngas stream 31 to the PSA unit 400 to produce a hydrogen stream 41 and a PSA off-gas stream 42; (g) recycling at least a portion of the PSA off-gas stream 42 to the reformer 150 for use as a fuel for heating the reformer 150; (h) introducing a second unshifted syngas stream 18b to the FT unit 500 to produce an FT product stream 52, an FT water stream 53, and an FT tail gas stream 51, wherein the second unshifted syngas stream 18b comprises a portion of the unshifted syngas stream 18, wherein the FT product can comprise FT liquids and FT wax, wherein the FT tail gas can comprise olefins, unreacted syngas, and carbon dioxide, and wherein the unreacted syngas can comprise carbon monoxide and hydrogen; (i) recycling at least a portion of the FT water stream 53 to the saturator 100 (for example via the water stream 11); (j) recycling a first FT tail gas stream 51a to the reformer 150 for use as a fuel for heating the reformer 150, wherein the first FT tail gas stream 51a comprises a portion (e.g., about 20%) of the FT tail gas stream 51; (k) introducing a second FT tail gas stream 51b and a steam stream 71 to the pre-reforming unit 700 to produce a pre-reformer effluent stream 72, wherein the second FT tail gas stream 51b comprises a portion (e.g., about 80%) of the FT tail gas stream 51, and wherein the pre-reformer effluent stream 72 comprises hydrogenated hydrocarbons; (l) introducing at least a portion of the pre-reformer effluent stream 72 to the reformer 150 (for example via the water saturated natural gas stream 15); and (m) introducing at least a portion of the FT product stream 52 and hydrogen to the hydrocracker 600 to produce a fuel stream 61 (e.g., diesel fuel, jet fuel, gasoline, etc.). The unshifted syngas stream 18, the second unshifted syngas stream 18b and/or the natural gas stream 10 can be optionally subjected to a sulfur removal step, as necessary, to avoid poisoning the FT catalyst. In an embodiment, the method of producing fuel from carbon dioxide can comprise generating at least one carbon credit from a reduction in emissions of carbon dioxide or a GHG having a carbon dioxide equivalency associated with consumed carbon dioxide of the recovered carbon dioxide fed to the reformer, wherein the reduction is at least 10%, alternatively at least 20%, alternatively at least 30%, alternatively at least 40%, alternatively at least 50%, alternatively at least 60%, alternatively at least 70%, alternatively at least 80%, alternatively at least 90%, alternatively from about 10% to about 90%, alternatively from about 15% to about 85%, or alternatively from about 20% to about 80%.

In an embodiment, a method of producing fuel from carbon dioxide as disclosed herein can advantageously display improvements in one or more method characteristics when compared to similar conventional methods of producing fuel. Conventional gas to liquids (GTL) processes using steam methane reformers usually result in excess $H_2$ in the syngas and a portion of the resulting syngas is normally underutilized as fuel in the reformer. The method of producing fuel from carbon dioxide as disclosed herein can advantageously react the excess hydrogen in the reformer with the recovered carbon dioxide that is added to the reformer to produce additional carbon monoxide, as previously described herein. FT tail gas contains unconverted $H_2$, and $H_2$ in the portion of the FT tail gas recycled to the reformer also facilitates the conversion of $CO_2$ to CO in the reformer. Production of additional carbon monoxide in the reformer can be advantageous because carbon monoxide is the source of carbon for the hydrocarbons produced in an FT process.

In an embodiment, a method of producing fuel from carbon dioxide as disclosed herein can advantageously utilize the FT water produced in the FT unit as steam for the reforming reaction by moisturizing a reformer feed gas using low level process heat. Conventionally, the FT water (e.g., FT aqueous condensate) in a typical GTL plant is subject to extensive, expensive treatment for reuse, due to the presence of trace hydrocarbons in the FT water.

In an embodiment, a method of producing fuel from carbon dioxide as disclosed herein can advantageously have an FT product yield (e.g., amount of fuel produced) increased by about 50% by the use of $CO_2$ to take advantage of the excess $H_2$ in the syngas produced in the reformer (when compared to an FT product yield of an otherwise similar method lacking introducing recovered carbon dioxide to the reformer). The loss of the $H_2$ in the fuel to the reformer is replaced with inexpensive natural gas with relatively low carbon foot print in the flue gas.

In an embodiment, a method of producing fuel from carbon dioxide as disclosed herein can advantageously reduce carbon emissions for an existing refinery, by utilizing waste $CO_2$ (e.g., recovered carbon dioxide, such as recycle carbon dioxide) from the refinery for a new GTL facility, which in turn could allow the existing refinery to install new refinery units without exceeding the carbon footprint of the existing refinery. Carbon emissions can be reduced from the refinery due to the use of carbon dioxide to produce transport fuels.

In an embodiment, a method of producing fuel from carbon dioxide as disclosed herein can advantageously allow for a GTL plant to have a net carbon dioxide emission rate of less than about 100,000 tons per year. Thus, the GTL plant could be classified as a small carbon emitter. Typically, 1,000 tons per day (tpd) of recycle of normally vented $CO_2$ can produce about 8,000 barrels per day incremental FT derived transport fuels. Conventionally, 1,000 tpd $CO_2$ can be vented from a refinery based $H_2$ plant incorporating a $CO_2$ removal unit with a capacity of about 55 MM standard cubic feet per day of $H_2$.

In an embodiment, a method of producing fuel from carbon dioxide as disclosed herein can advantageously employ modular systems, thereby minimizing construction activities at a plant site and reducing installation costs. For example, a modular (e.g., portable) unit could be installed to address $CO_2$ emissions from a temporary source (e.g., a seasonal or temporary industrial worksite that produces $CO_2$ emissions, for example via one or more combustion powered units, processes, systems, etc.).

In an embodiment, a method of producing fuel from carbon dioxide as disclosed herein can advantageously increase an overall thermal efficiency of converting natural gas to transport fuels from about 55-60% (without the $CO_2$ addition to the reformer) to about 65-70% (with the $CO_2$ addition to the reformer). Addition of carbon dioxide (e.g., recovered carbon dioxide) to the reformer can advantageously allow for reducing a reformer steam requirement, thereby avoiding use of expensive steam using instead the FT water via moisturization (e.g., for example in a saturator). A higher (e.g., increased) thermal efficiency can be due to conversion of valuable excess $H_2$ (which otherwise would be used as fuel) to carbon monoxide by reaction with waste $CO_2$ (e.g., recovered $CO_2$), and can also be due to using an existing hydrocracker in the refinery. Additional advantages of the methods of producing fuel from carbon dioxide as disclosed herein can be apparent to one of skill in the art viewing this disclosure.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggested to one of ordinary skill in the art without departing from the spirit of the present invention or the scope of the appended claims.

Additional Disclosure

A first embodiment, which is a method of producing fuel from carbon dioxide comprising (a) introducing natural gas, steam, and recovered carbon dioxide to a reformer to produce unshifted synthesis gas (syngas), wherein the unshifted syngas is characterized by a molar ratio of hydrogen to carbon monoxide of from about 1.7:1 to about 2.5:1, and wherein the reformer is a new reformer, an existing reformer, or combinations thereof; (b) introducing a portion of the unshifted syngas to a water gas shift unit to produce a shifted syngas, wherein a molar ratio of hydrogen to carbon monoxide in the shifted syngas is greater than a molar ratio of hydrogen to carbon monoxide in the unshifted syngas, wherein an amount of carbon dioxide in the shifted syngas is greater than an amount of carbon dioxide in the unshifted syngas, and wherein the water gas shift unit is a new water gas shift unit, an existing water gas shift unit, or combinations thereof; (c) separating at least a portion of the carbon dioxide from at least a portion of the shifted syngas in a carbon dioxide recovery unit to produce recycle carbon dioxide and a hydrogen-enriched syngas, wherein the carbon dioxide recovery unit is a new carbon dioxide recovery unit, an existing carbon dioxide recovery unit, or combinations thereof; (d) recycling at least a portion of the recycle carbon dioxide to the reformer; (e) introducing a portion of the unshifted syngas to a Fischer-Tropsch (FT) unit to produce an FT product, FT water, and FT tail gas, wherein the FT product comprises FT liquids and FT wax; and (f) separating at least a portion of the FT liquids from at least a portion of the FT product to produce a fuel.

A second embodiment, which is the method of the first embodiment, wherein at least a portion of the natural gas is contacted with steam and/or FT water in a saturator prior to introducing the natural gas to the reformer.

A third embodiment, which is the method of any one of the first and the second embodiments, wherein the FT water comprises water and hydrocarbons, wherein at least a portion of the FT water is used for producing the steam that is introduced to the reformer, and wherein at least a portion of the hydrocarbons of the FT water is converted to syngas in the reformer.

A fourth embodiment, which is the method of any one of the first through the third embodiments further excluding treating the FT water for hydrocarbon removal.

A fifth embodiment, which is the method of any one of the first through the fourth embodiments, wherein a portion of the FT tail gas is used as fuel for heating the reformer and/or a pre-reforming unit.

A sixth embodiment, which is the method of any one of the first through the fifth embodiments, wherein from about 5 vol. % to about 35 vol. % of the FT tail gas is used as fuel for heating the reformer and/or a pre-reforming unit.

A seventh embodiment, which is the method of any one of first through the sixth embodiments, wherein the FT tail gas comprises olefins and unreacted syngas, wherein the unreacted syngas comprises carbon monoxide and hydrogen, wherein at least a portion of the FT tail gas and steam are introduced to a pre-reformer to produce hydrogenated hydrocarbons, wherein at least a portion of the olefins react with at least a portion of the hydrogen to produce the hydrogenated hydrocarbons.

An eighth embodiment, which is the method of the seventh embodiment, wherein at least a portion of the hydrogenated hydrocarbons are introduced to the reformer.

A ninth embodiment, which is the method of the eighth embodiment, wherein at least a portion of the hydrogenated hydrocarbons is converted to syngas in the reformer.

A tenth embodiment, which is the method of any one of first through the ninth embodiments, wherein from about 65 vol. % to about 95 vol. % of the FT tail gas is introduced to the pre-reformer to produce the hydrogenated hydrocarbons.

An eleventh embodiment, which is the method of any one of the first through the tenth embodiments further comprising introducing at least a portion of the FT product and hydrogen to a hydrocracker, wherein the hydrocracker is a new hydrocracker, an existing hydrocracker, or combinations thereof.

A twelfth embodiment, which is the method of any one of the first through the eleventh embodiments further comprising recovering at least a portion of the FT wax from the FT product and introducing at least a portion of the FT wax to a hydrocracker, wherein the hydrocracker is a new hydrocracker, an existing hydrocracker, or combinations thereof.

A thirteenth embodiment, which is the method of any one of the first through the twelfth embodiments, wherein the fuel comprises diesel fuel, jet fuel, gasoline, or combinations thereof.

A fourteenth embodiment, which is the method of any one of the first through the thirteenth embodiments, wherein at least a portion of the hydrogen-enriched syngas is introduced to a pressure swing adsorption (PSA) unit to produce hydrogen and a PSA off-gas, and wherein the hydrocracker is a new PSA unit, an existing PSA unit, or combinations thereof.

A fifteenth embodiment, which is the method of the fourteenth embodiment, wherein at least a portion of the PSA off-gas is used as fuel for heating the reformer.

A sixteenth embodiment, which is the method of any one of the first through the fifteenth embodiments, wherein at least a portion of the hydrogen is introduced to a hydrocracker, and wherein the hydrocracker is a new hydrocracker, an existing hydrocracker, or combinations thereof.

A seventeenth embodiment, which is the method of any one of the first through the sixteenth embodiments, wherein a molar ratio of carbon dioxide to methane in the total feed streams to the reformer is from about 0.5:1 to about 1.5:1.

An eighteenth embodiment, which is the method of any one of the first through the seventeenth embodiments, wherein a molar ratio of steam to methane in the total feed streams to the reformer is from about 0.75:1 to about 3.0:1.

A nineteenth embodiment, which is the method of any one of the first through the eighteenth embodiments, wherein the natural gas further comprises carbon dioxide, and wherein the method excludes separating at least a portion of the carbon dioxide from the natural gas prior to introducing the natural gas to the reformer.

A twentieth embodiment, which is the method of any one of the first through the nineteenth embodiments, wherein the reformer comprises a nickel-based catalyst and/or a sulfur passivated nickel-based catalyst.

A twenty-first embodiment, which is the method of any one of the first through the twentieth embodiments, wherein an amount of fuel produced is increased by equal to or greater than about 30% when compared to an amount of fuel produced by an otherwise similar method lacking introducing recovered carbon dioxide to the reformer.

A twenty-second embodiment, which is the method any one of the first through the twenty-first embodiments, wherein at least a portion of the recovered carbon dioxide that is introduced to the reformer is converted to the fuel.

A twenty-third embodiment, which is the method of any one of the first through the twenty-second embodiments further comprising generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is at least 10%.

A twenty-fourth embodiment, which is the method of the twenty-third embodiment, wherein an economic benefit is received from monetizing the at least one carbon credit.

A twenty-fifth embodiment, which is the method of any one of the first through the twenty-fourth embodiments, wherein the at least one carbon credit is traded on a public exchange.

A twenty-sixth embodiment, which is the method of any one of the first through the twenty-fifth embodiments, wherein at least a portion of the at least one carbon credit is used as an offset for an industrial gas-producing process.

A twenty-seventh embodiment, which is the method of any one of the first through the twenty-sixth embodiments, wherein the recovered carbon dioxide comprises at least a portion of the recycle carbon dioxide.

A twenty-eighth embodiment, which is a method of producing fuel from carbon dioxide comprising (a) introducing natural gas, steam, and recovered carbon dioxide to a reformer to produce unshifted synthesis gas (syngas), wherein at least a portion of the recovered carbon dioxide is converted to carbon monoxide, and wherein the unshifted syngas is characterized by a molar ratio of hydrogen to carbon monoxide of from about 1.7:1 to about 2.5:1; (b) introducing a portion of the unshifted syngas to a Fischer-Tropsch (FT) unit to produce an FT product, FT water, and FT tail gas, wherein the FT product comprises FT liquids and FT wax; (c) separating at least a portion of the FT liquids from at least a portion of the FT product to produce a fuel; and (d) generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is from about 10% to about 90%.

A twenty-ninth embodiment, which is the method of the twenty-eighth embodiment further comprising receiving an economic benefit from monetizing the at least one carbon credit.

A thirtieth embodiment, which is the method of any one of the twenty-eighth and the twenty-ninth embodiments, wherein the recovered carbon dioxide comprises carbon dioxide recovered from a flue gas, a reformer flue gas, a shifted syngas, a carbon dioxide pipeline, associated gas from oil fields, an exhaust gas from fuel combustion in an industrial combustion device, unit, or system, a refinery vent stream, a natural gas, or combinations thereof.

A thirty-first embodiment, which is the method of any one of the twenty-eighth through the thirtieth embodiments, wherein the recovered carbon dioxide comprises carbon dioxide recovered from a reformer flue gas using an amine solvent absorption and stripping system.

A thirty-second embodiment, which is a method of producing fuel from carbon dioxide comprising (a) introducing natural gas, steam, and recovered carbon dioxide to a reformer to produce unshifted synthesis gas (syngas), wherein at least a portion of the recovered carbon dioxide is converted to carbon monoxide, and wherein the unshifted syngas is characterized by a molar ratio of hydrogen to carbon monoxide of from about 1.7:1 to about 2.5:1; (b) introducing a first portion of the unshifted syngas to a water gas shift unit to produce a shifted syngas, wherein a molar ratio of hydrogen to carbon monoxide in the shifted syngas is greater than a molar ratio of hydrogen to carbon monoxide in the unshifted syngas, and wherein an amount of carbon dioxide in the shifted syngas is greater than an amount of carbon dioxide in the unshifted syngas; (c) separating at least a portion of the carbon dioxide from at least a portion of the shifted syngas to produce recycle carbon dioxide and a hydrogen-enriched syngas; (d) recycling at least a portion of the recycle carbon dioxide to the reformer; (e) introducing a second portion of the unshifted syngas to a Fischer-Tropsch (FT) unit to produce an FT product, FT water, and FT tail gas, wherein the FT product comprises FT liquids and FT wax; (f) separating at least a portion of the FT liquids from at least a portion of the FT product to produce a fuel; and (g) generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is at least 10%.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A method of producing fuel from carbon dioxide comprising:

(a) introducing natural gas, steam, and recovered carbon dioxide to a reformer to produce unshifted synthesis gas (syngas), wherein the unshifted syngas is characterized by a molar ratio of hydrogen to carbon monoxide of from about 1.7:1 to about 2.5:1, and wherein the reformer is a new reformer, an existing reformer, or combinations thereof;
    (b) introducing a portion of the unshifted syngas to a water gas shift unit to produce a shifted syngas, wherein a molar ratio of hydrogen to carbon monoxide in the shifted syngas is greater than a molar ratio of hydrogen to carbon monoxide in the unshifted syngas, wherein an amount of carbon dioxide in the shifted syngas is greater than an amount of carbon dioxide in the unshifted syngas, and wherein the water gas shift unit is a new water gas shift unit, an existing water gas shift unit, or combinations thereof;
    (c) separating at least a portion of the carbon dioxide from at least a portion of the shifted syngas in a carbon dioxide recovery unit to produce recycle carbon dioxide and a hydrogen-enriched syngas, wherein the carbon dioxide recovery unit is a new carbon dioxide recovery unit, an existing carbon dioxide recovery unit, or combinations thereof;
    (d) recycling at least a portion of the recycle carbon dioxide to the reformer;
    (e) introducing a portion of the unshifted syngas to a Fischer-Tropsch (FT) unit to produce an FT product, FT water, and FT tail gas, wherein the FT product comprises FT liquids and FT wax; and
    (f) separating at least a portion of the FT liquids from at least a portion of the FT product to produce a fuel.

2. The method of claim 1, wherein at least a portion of the natural gas is contacted with steam and/or FT water in a saturator prior to introducing the natural gas to the reformer.

3. The method of claim 1, wherein the FT water comprises water and hydrocarbons, wherein at least a portion of the FT water is used for producing the steam that is introduced to the reformer, and wherein at least a portion of the hydrocarbons of the FT water is converted to syngas in the reformer.

4. The method of claim 1 further excluding treating the FT water for hydrocarbon removal.

5. The method of claim 1, wherein a portion of the FT tail gas is used as fuel for heating the reformer and/or a pre-reforming unit.

6. The method of claim 1, wherein from about 5 vol. % to about 35 vol. % of the FT tail gas is used as fuel for heating the reformer and/or a pre-reforming unit.

7. The method of claim 1, wherein the FT tail gas comprises olefins and unreacted syngas, wherein the unreacted syngas comprises carbon monoxide and hydrogen, wherein at least a portion of the FT tail gas and steam are introduced to a pre-reformer to produce hydrogenated hydrocarbons, wherein at least a portion of the olefins react with at least a portion of the hydrogen to produce the hydrogenated hydrocarbons.

8. The method of claim 7, wherein at least a portion of the hydrogenated hydrocarbons are introduced to the reformer.

9. The method of claim 8, wherein at least a portion of the hydrogenated hydrocarbons is converted to syngas in the reformer.

10. The method of claim 7, wherein from about 65 vol. % to about 95 vol. % of the FT tail gas is introduced to the pre-reformer to produce the hydrogenated hydrocarbons.

11. The method of claim 1 further comprising introducing at least a portion of the FT product and hydrogen to a hydrocracker, wherein the hydrocracker is a new hydrocracker, an existing hydrocracker, or combinations thereof.

12. The method of claim 1 further comprising recovering at least a portion of the FT wax from the FT product and introducing at least a portion of the FT wax to a hydrocracker, wherein the hydrocracker is a new hydrocracker, an existing hydrocracker, or combinations thereof.

13. The method of claim 1, wherein the fuel comprises diesel fuel, jet fuel, gasoline, or combinations thereof.

14. The method of claim 1, wherein at least a portion of the hydrogen-enriched syngas is introduced to a pressure swing adsorption (PSA) unit to produce hydrogen and a PSA off-gas, and wherein the PSA unit is a new PSA unit, an existing PSA unit, or combinations thereof.

15. The method of claim 14, wherein at least a portion of the PSA off-gas is used as fuel for heating the reformer.

16. The method of claim 14, wherein at least a portion of the hydrogen is introduced to a hydrocracker, and wherein the hydrocracker is a new hydrocracker, an existing hydrocracker, or combinations thereof.

17. The method of claim 1, wherein a molar ratio of carbon dioxide to methane in the total feed streams to the reformer is from about 0.5:1 to about 1.5:1.

18. The method of claim 1, wherein a molar ratio of steam to methane in the total feed streams to the reformer is from about 0.75:1 to about 3.0:1.

19. The method of claim 1, wherein the natural gas further comprises carbon dioxide, and wherein the method excludes separating at least a portion of the carbon dioxide from the natural gas prior to introducing the natural gas to the reformer.

20. The method of claim 1, wherein the reformer comprises a nickel-based catalyst and/or a sulfur passivated nickel-based catalyst.

21. The method of claim 1, wherein an amount of fuel produced is increased by equal to or greater than about 30% when compared to an amount of fuel produced by an otherwise similar method lacking introducing recovered carbon dioxide to the reformer.

22. The method of claim 1, wherein at least a portion of the recovered carbon dioxide that is introduced to the reformer is converted to the fuel.

23. The method of claim 1 further comprising generating at least one carbon credit from a reduction in emissions of carbon dioxide or a greenhouse gas (GHG) having a carbon dioxide equivalency associated with consumed carbon dioxide of the recovered carbon dioxide fed to the reformer, wherein the reduction is at least 10%.

24. The method of claim 23, wherein an economic benefit is received from monetizing the at least one carbon credit.

25. The method of claim 23, wherein the at least one carbon credit is traded on a public exchange.

26. The method of claim 23, wherein at least a portion of the at least one carbon credit is used as an offset for an industrial gas-producing process.

27. The method of claim 1, wherein the recovered carbon dioxide comprises at least a portion of the recycle carbon dioxide.

* * * * *